United States Patent
Brett

(10) Patent No.: US 8,932,359 B2
(45) Date of Patent: Jan. 13, 2015

(54) INTERVERTEBRAL IMPLANT HAVING EXTENDABLE BONE FIXATION MEMBERS

(71) Applicant: Expanding Concepts, LLC, Portland, OR (US)

(72) Inventor: Darrell C. Brett, Portland, OR (US)

(73) Assignee: Expanding Concepts, LLC, Portland, OR (US)

( * ) Notice: Subject to any disclaimer, the term of this patent is extended or adjusted under 35 U.S.C. 154(b) by 0 days.

(21) Appl. No.: 14/064,434

(22) Filed: Oct. 28, 2013

(65) Prior Publication Data

US 2014/0052262 A1    Feb. 20, 2014

Related U.S. Application Data

(62) Division of application No. 12/884,664, filed on Sep. 17, 2010, now Pat. No. 8,617,245.

(60) Provisional application No. 61/243,297, filed on Sep. 17, 2009, provisional application No. 61/260,364, filed on Nov. 11, 2009.

(51) Int. Cl.
*A61F 2/44* (2006.01)
*A61F 2/46* (2006.01)
(Continued)

(52) U.S. Cl.
CPC ............ *A61F 2/442* (2013.01); *A61F 2/4465* (2013.01); *A61F 2/4611* (2013.01); *A61F 2002/2835* (2013.01); *A61F 2002/30507* (2013.01);
(Continued)

(58) Field of Classification Search
USPC .......................................... 623/17.11–17.16
See application file for complete search history.

(56) References Cited

U.S. PATENT DOCUMENTS

| | | |
|---|---|---|
| 3,791,380 A | 2/1974 | Dawidowski |
| 3,875,595 A | 4/1975 | Froning |

(Continued)

FOREIGN PATENT DOCUMENTS

| | | |
|---|---|---|
| DE | 4327054 | 4/1995 |
| EP | 0260044 | 3/1988 |

(Continued)

OTHER PUBLICATIONS

Synthes, "Synthes Global Interent: SynFix-LR", http://www.synthes.com/html/SynFix-LR.6902.0.html, .COPYRGT. 2009, accessed Sep. 16, 2009, 1page. cited by applicant.

(Continued)

*Primary Examiner* — Sameh Boles
(74) *Attorney, Agent, or Firm* — Law Office of Karen Dana Oster LLC

(57) ABSTRACT

An intervertebral implant is configured to be fixed in an intervertebral space defined by a first vertebral body and a second vertebral body. The intervertebral implant includes an implant body sized to be inserted into an intervertebral space, and a fixation assembly configured to be attached to the implant body. The fixation assembly includes a housing that defines a first vertebral body facing surface and a second vertebral body facing surface spaced from the first vertebral body facing surface along a transverse direction. The fixation assembly further includes at least one fixation member supported by the housing and movable from a retracted position to an extended position, whereby in the extended position the fixation member extends out from the housing and into one of the vertebral bodies.

37 Claims, 38 Drawing Sheets

(51) Int. Cl.
*A61F 2/28* (2006.01)
*A61F 2/30* (2006.01)

(52) U.S. Cl.
CPC .............. *A61F2002/30518* (2013.01); *A61F 2002/30525* (2013.01); *A61F 2002/30579* (2013.01); *A61F 2220/0025* (2013.01); *A61F 2310/00017* (2013.01); *A61F 2310/00023* (2013.01); *A61F 2310/00029* (2013.01); *A61F 2310/00179* (2013.01); *A61F 2310/00796* (2013.01)
USPC .................................................. 623/17.16

(56) References Cited

U.S. PATENT DOCUMENTS

| | | | |
|---|---|---|---|
| 3,948,262 A | 4/1976 | Zaffaroni | |
| 4,349,921 A | 9/1982 | Kuntz | |
| 4,507,115 A | 3/1985 | Kambara et al. | |
| 4,599,086 A | 7/1986 | Doty | |
| 4,714,469 A | 12/1987 | Kenna | |
| 4,721,103 A | 1/1988 | Freedland | |
| 4,790,303 A | 12/1988 | Steffee | |
| 4,834,757 A | 5/1989 | Brantigan | |
| 5,658,335 A | 8/1997 | Allen | |
| 5,683,394 A | 11/1997 | Rinner | |
| 5,800,547 A | 9/1998 | Schafer et al. | |
| 5,800,550 A | 9/1998 | Sertich | |
| 5,810,820 A | 9/1998 | Santori et al. | |
| 5,849,004 A * | 12/1998 | Bramlet | 606/232 |
| 5,888,228 A | 3/1999 | Knothe et al. | |
| 6,113,638 A | 9/2000 | Williams et al. | |
| 6,179,873 B1 | 1/2001 | Zientek | |
| 6,210,442 B1 | 4/2001 | Wing et al. | |
| 6,214,050 B1 | 4/2001 | Huene | |
| 6,231,610 B1 | 5/2001 | Geisler | |
| 6,235,059 B1 | 5/2001 | Benezech et al. | |
| 6,258,089 B1 | 7/2001 | Campbell et al. | |
| 6,364,880 B1 | 4/2002 | Michelson | |
| 6,371,987 B1 | 4/2002 | Weiland et al. | |
| 6,383,186 B1 | 5/2002 | Michelson | |
| 6,423,063 B1 | 7/2002 | Bonutti | |
| 6,447,546 B1 | 9/2002 | Bramlet et al. | |
| 6,527,803 B1 | 3/2003 | Crozet et al. | |
| 6,558,423 B1 | 5/2003 | Michelson | |
| 6,620,163 B1 | 9/2003 | Michelson | |
| 6,695,846 B2 | 2/2004 | Richelsoph et al. | |
| 6,712,818 B1 | 3/2004 | Michelson | |
| 6,767,367 B1 | 7/2004 | Michelson | |
| 6,770,096 B2 | 8/2004 | Bolger et al. | |
| 6,800,092 B1 | 10/2004 | Williams et al. | |
| 6,923,830 B2 | 8/2005 | Michelson | |
| 6,981,975 B2 | 1/2006 | Michelson | |
| 7,051,610 B2 | 5/2006 | Stoianovici et al. | |
| 7,112,206 B2 | 9/2006 | Michelson | |
| 7,137,984 B2 | 11/2006 | Michelson | |
| 7,223,289 B2 | 5/2007 | Trieu et al. | |
| 7,255,698 B2 | 8/2007 | Michelson | |
| 7,303,583 B1 | 12/2007 | Schar et al. | |
| 7,455,684 B2 | 11/2008 | Gradel et al. | |
| 7,473,276 B2 | 1/2009 | Aebi et al. | |
| 7,563,284 B2 | 7/2009 | Coppes et al. | |
| 7,563,286 B2 | 7/2009 | Gerber et al. | |
| 7,594,932 B2 | 9/2009 | Aferzon et al. | |
| 7,846,188 B2 | 12/2010 | Moskowitz et al. | |
| 8,075,618 B2 | 12/2011 | Trieu et al. | |
| 8,080,062 B2 | 12/2011 | Armstrong et al. | |
| 8,257,443 B2 | 9/2012 | Kamran et al. | |
| 8,303,663 B2 | 11/2012 | Jimenez et al. | |
| 8,313,528 B1 | 11/2012 | Wensel | |
| 8,323,345 B2 | 12/2012 | Sledge | |
| 8,343,197 B2 | 1/2013 | Gonzalez-Hernandez | |
| 8,353,219 B2 | 1/2013 | Brackett et al. | |
| 8,535,352 B2 | 9/2013 | Altarac et al. | |
| 8,545,563 B2 | 10/2013 | Brun et al. | |
| 8,617,245 B2 | 12/2013 | Brett | |
| 2002/0059938 A1 | 5/2002 | Fogarty et al. | |
| 2003/0149484 A1 | 8/2003 | Michelson | |
| 2003/0187436 A1 | 10/2003 | Bolger et al. | |
| 2004/0010312 A1 | 1/2004 | Enayati | |
| 2005/0027362 A1 | 2/2005 | Williams et al. | |
| 2005/0049590 A1 | 3/2005 | Alleyne et al. | |
| 2005/0143825 A1 | 6/2005 | Enayati | |
| 2005/0283236 A1 | 12/2005 | Razian | |
| 2006/0085071 A1 | 4/2006 | Lechmann et al. | |
| 2006/0095136 A1 | 5/2006 | McLuen | |
| 2006/0241621 A1 | 10/2006 | Moskowitz et al. | |
| 2006/0241764 A1 | 10/2006 | Michelson | |
| 2006/0253201 A1 | 11/2006 | McLuen | |
| 2006/0276899 A1 | 12/2006 | Zipnick et al. | |
| 2007/0049943 A1 | 3/2007 | Moskowitz et al. | |
| 2007/0106388 A1 | 5/2007 | Michelson | |
| 2007/0179623 A1 | 8/2007 | Trieu et al. | |
| 2007/0208345 A1 | 9/2007 | Marnay et al. | |
| 2007/0270960 A1 | 11/2007 | Bonin et al. | |
| 2007/0270961 A1 | 11/2007 | Ferguson | |
| 2008/0033432 A1 | 2/2008 | McGraw et al. | |
| 2008/0132949 A1 | 6/2008 | Aferzon et al. | |
| 2008/0177306 A1 | 7/2008 | Lamborne et al. | |
| 2009/0099601 A1 | 4/2009 | Aferzon et al. | |
| 2009/0112271 A1 | 4/2009 | Moskowitz et al. | |
| 2009/0118771 A1 | 5/2009 | Gonzalez-Hernandez | |
| 2009/0164020 A1 | 6/2009 | Janowski et al. | |
| 2009/0265007 A1 | 10/2009 | Colleran | |
| 2010/0016974 A1 | 1/2010 | Janowski et al. | |
| 2010/0050276 A1 | 2/2010 | DePaepe | |
| 2010/0057206 A1 | 3/2010 | Duffield et al. | |
| 2010/0161057 A1 | 6/2010 | Berry et al. | |
| 2010/0185289 A1 | 7/2010 | Kirwan et al. | |
| 2010/0298941 A1 | 11/2010 | Hes et al. | |
| 2010/0312345 A1 | 12/2010 | Duffield et al. | |
| 2010/0312346 A1 | 12/2010 | Kueenzi et al. | |
| 2011/0054616 A1 | 3/2011 | Kamran et al. | |
| 2011/0112587 A1 | 5/2011 | Patel et al. | |
| 2011/0178599 A1 | 7/2011 | Brett | |
| 2011/0208311 A1 | 8/2011 | Janowski | |
| 2011/0230971 A1 | 9/2011 | Donner et al. | |
| 2012/0022654 A1 | 1/2012 | Farris et al. | |
| 2012/0197404 A1 | 8/2012 | Brun et al. | |

FOREIGN PATENT DOCUMENTS

| | | |
|---|---|---|
| EP | 0667127 | 9/1995 |
| EP | 2047825 | 4/2009 |
| FR | 2779941 | 12/1999 |
| JP | 03-505416 | 11/1991 |
| WO | WO90/00037 | 1/1990 |
| WO | WO/95/25469 | 3/1995 |
| WO | WO9966867 | 12/1999 |
| WO | WO2004080356 | 9/2004 |
| WO | WO2007098288 | 8/2007 |
| WO | WO2007127771 | 11/2007 |
| WO | WO2008044057 | 4/2008 |
| WO | WO2008102174 | 8/2008 |
| WO | WO2009004625 | 1/2009 |
| WO | WO2009070721 | 6/2009 |
| WO | WO2009131955 | 10/2009 |
| WO | WO2010121028 | 10/2010 |
| WO | WO2011129973 | 10/2011 |

OTHER PUBLICATIONS

International Search Report and the Written Opinion, The International Searching Authority, Patent Cooperation Treaty, PCT/US2010/049287; Jan. 11, 2011, 6 pages.

Nakamura & Partners, Patent Trademark and Legal Affairs, communication regarding Japanese Patent Application No. 2012-529931, dated Jun. 3, 2014, Tokyo, Japan, 14 pages.

* cited by examiner

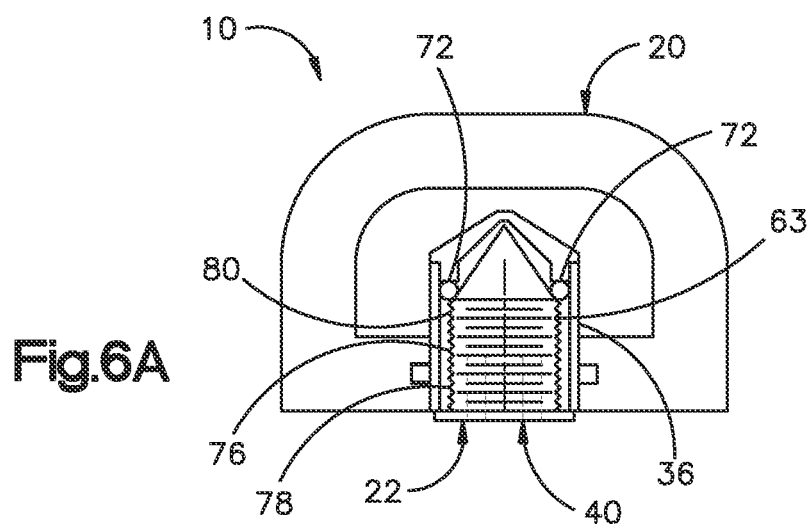
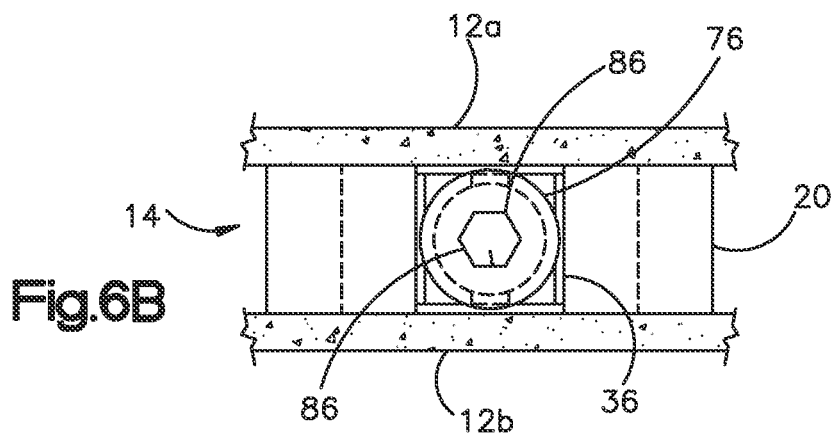
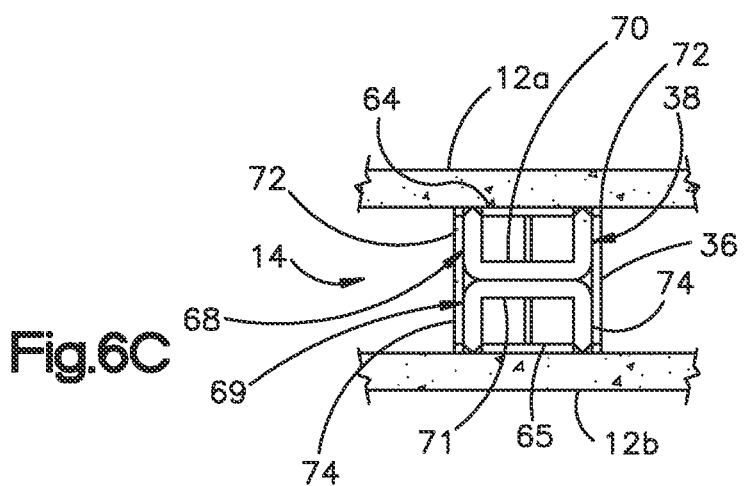

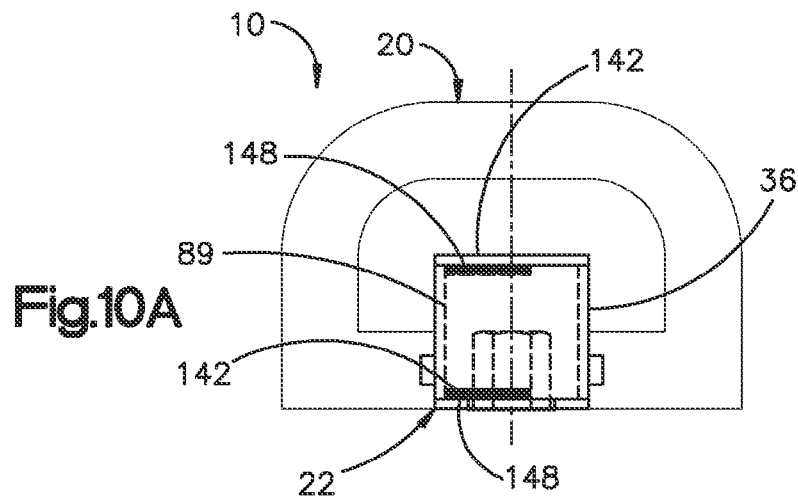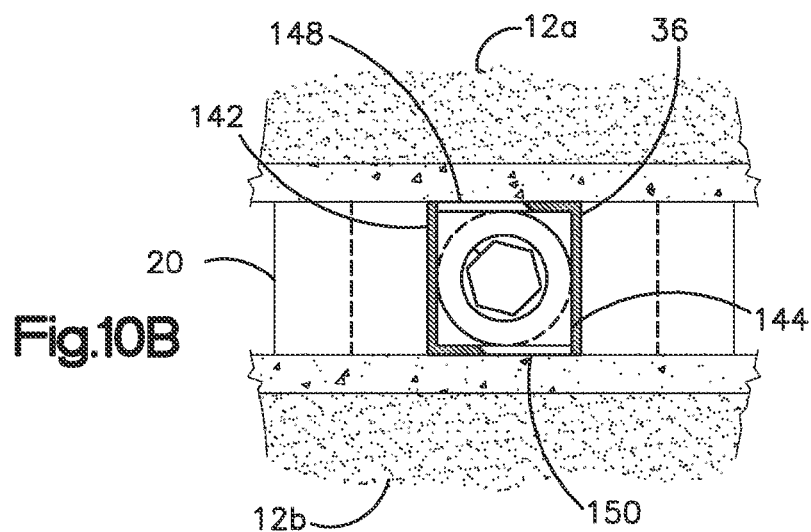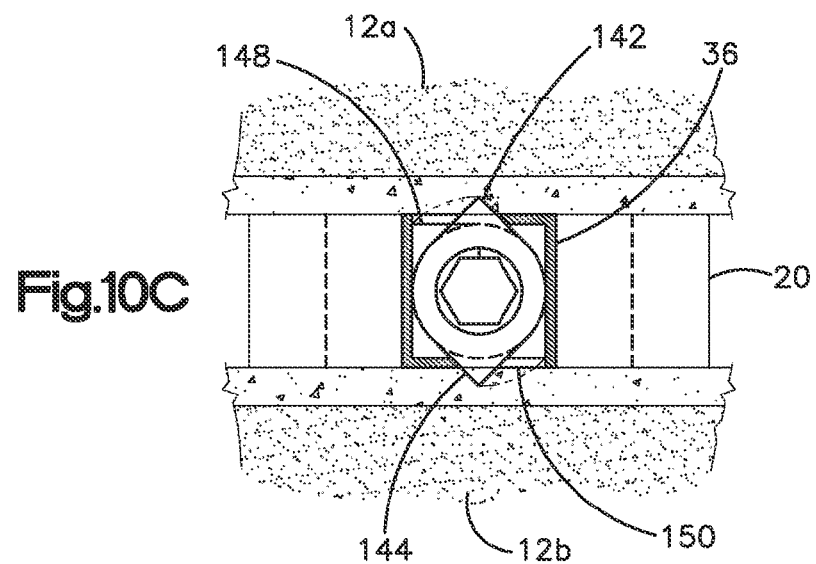

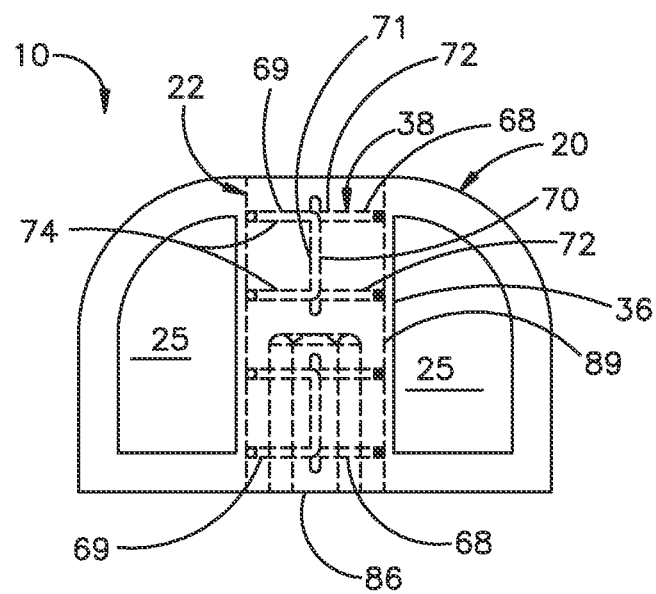
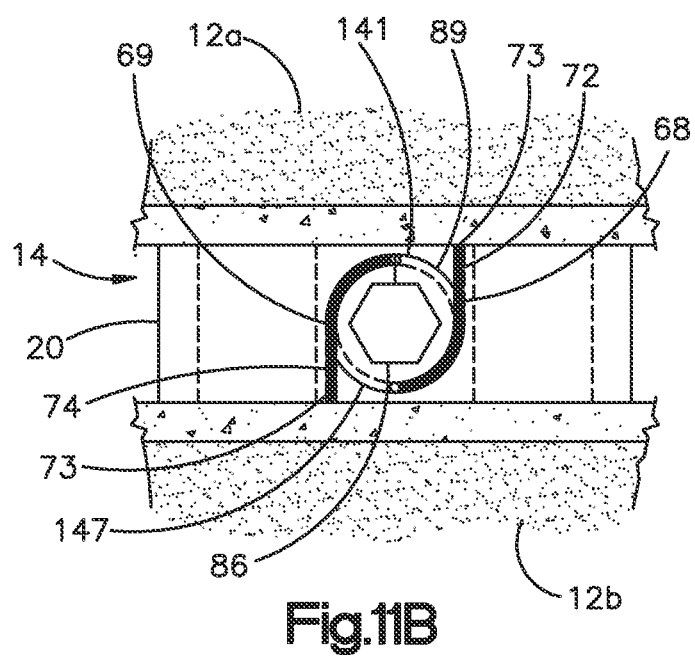

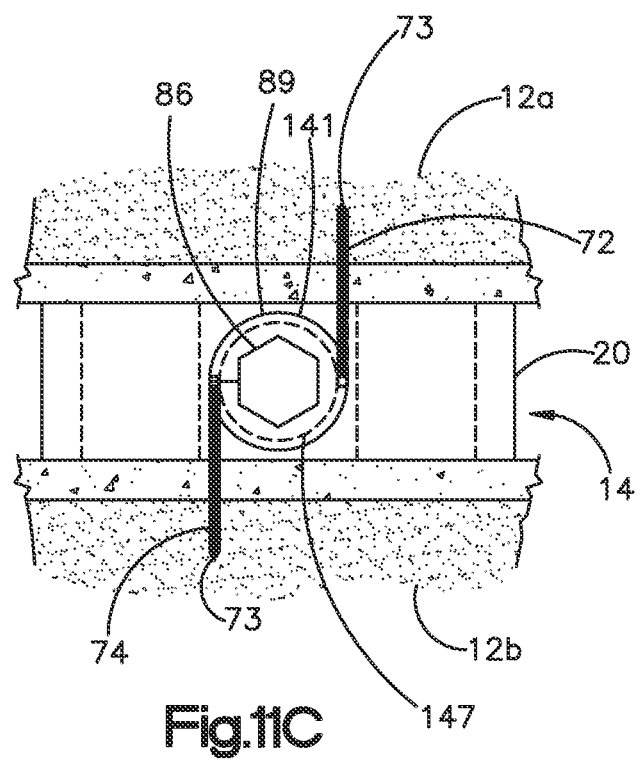

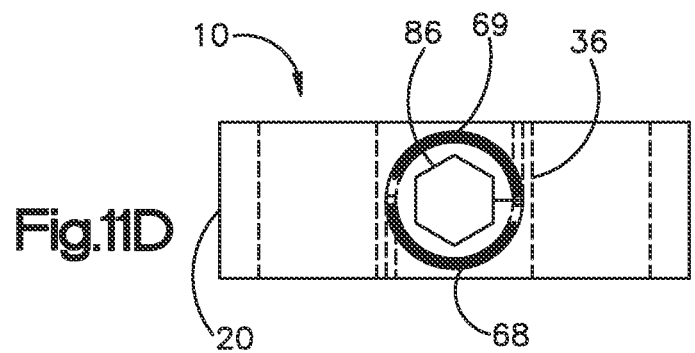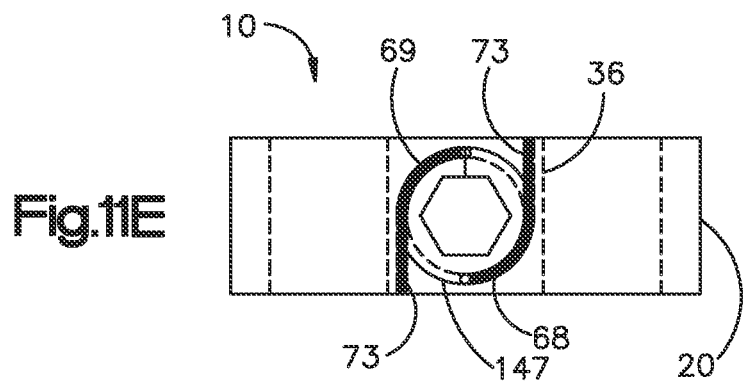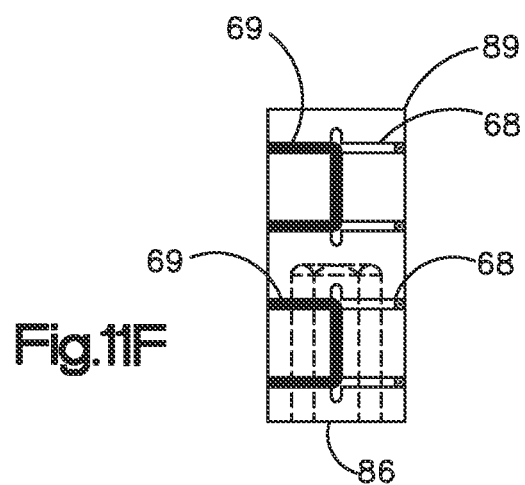

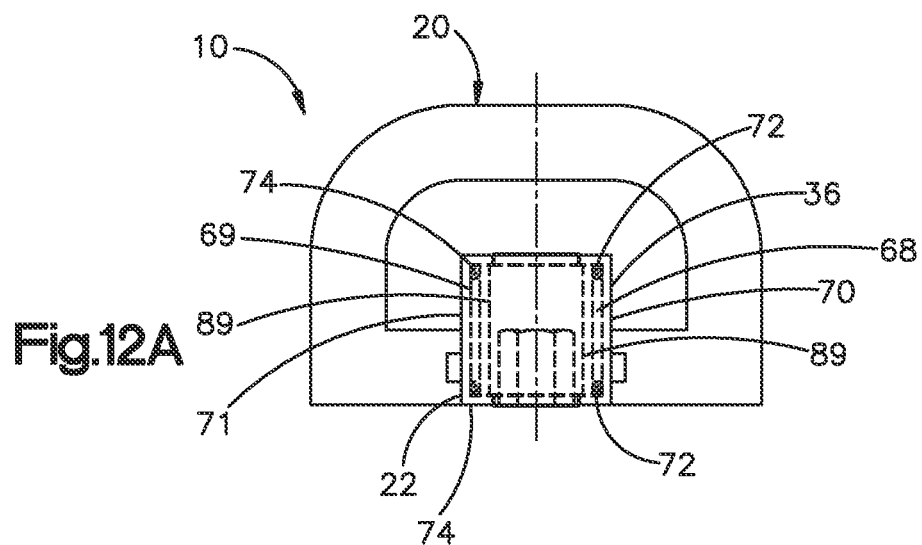
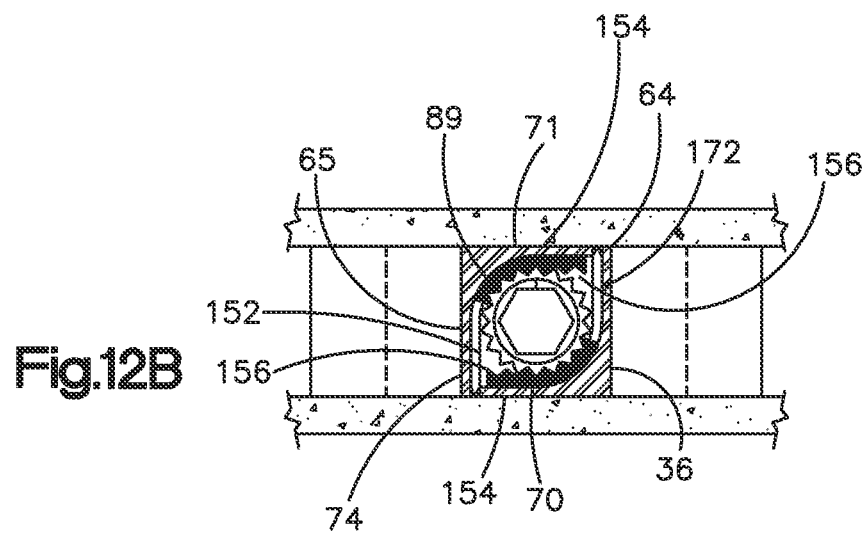
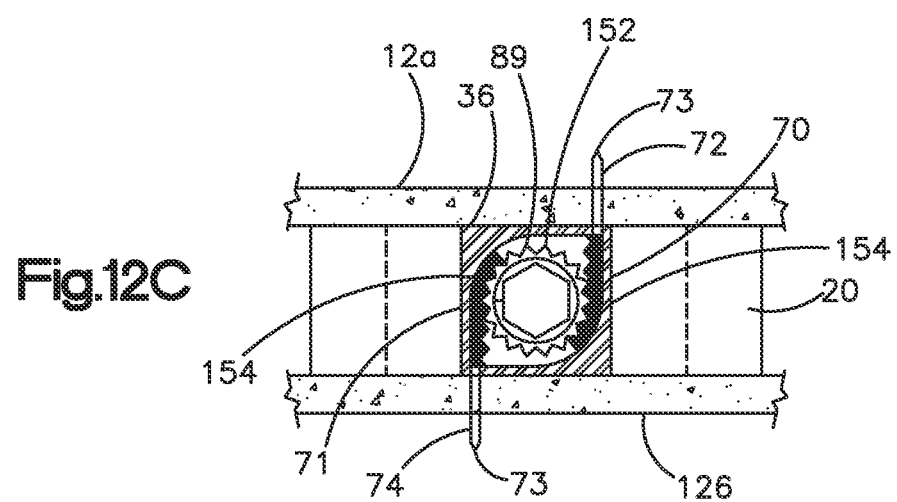

INTERVERTEBRAL IMPLANT HAVING EXTENDABLE BONE FIXATION MEMBERS

CROSS-REFERENCE TO RELATED APPLICATIONS

This application is a divisional of pending U.S. patent application Ser. No. 12/884,664 filed Sep. 17, 2010, which claims the benefit of U.S. Provisional Patent Application Ser. No. 61/243,297 filed Sep. 17, 2009, and further claims the benefit of U.S. Provisional Patent Application Ser. No. 61/260,364 filed Nov. 11, 2009. The disclosure of each application listed in this paragraph is hereby incorporated by reference as if set forth in its entirety herein.

BACKGROUND

The human vertebral column (also known as the backbone or spine) houses the spinal cord in its spinal canal. The vertebral column is made up of a plurality of vertebrae. A typical vertebra includes two primary parts, including an anterior portion that includes the vertebral body, and a posterior portion that encloses the foramen. Each vertebral body defines superior and inferior vertebral endplates that, such that adjacent vertebrae define an intervertebral space that includes disc material between the respective endplates.

Historically, spinal abnormalities have indicated complete removal of a disc from the intervertebral space followed by fusion the adjacent vertebrae together. This "spinal fusion" procedure, which is still in use today, is a widely accepted surgical treatment for symptomatic lumbar and cervical degenerative disc disease. Early fusion procedures used an implant made of bone from a patient's hip or a cadaver bone as a spacer in the intervertebral space so as to properly position the adjacent vertebrae until the vertebrae were fused together. More modern procedures use implants made from a material having a relatively low modulus of elasticity to encourage bone growth. For instance, the implant can contain some of the patient's own bone, e.g., within apertures of the implant. Conventional implants can be made from desired material, including radiolucent materials such as polyetheretherketone (PEEK), ultra-high molecular weight polyethylenes (UHMWPE) or polysulfones (PSU). It can be desirable for the material to have a modulus of elasticity between 3 and 5 GPa.

Conventional intervertebral implant designs have attempted to achieve implant fixation in the intervertebral space.

SUMMARY

In accordance with one embodiment, an intervertebral implant is configured to be fixed in an intervertebral space defined by a first vertebral body and a second vertebral body. The intervertebral implant includes an implant body sized to be inserted into an intervertebral space, and a fixation assembly configured to be attached to the implant body. The fixation assembly includes a housing that defines a first vertebral body facing surface and a second vertebral body facing surface spaced from the first vertebral body facing surface along a transverse direction. The housing defines a channel. The fixation assembly further includes a first superior staple and a second inferior staple that is transversely opposite the first superior staple. Each staple is supported in the channel such that each staple includes a crossbar and a pair of spaced that extend transversely out from the crossbar. Each crossbar defines respective first and second cam surfaces. The intervertebral implant further includes an actuator that is configured to translate along a distal direction within the housing that is substantially orthogonal to the transverse direction. The actuator is configured to substantially simultaneously engage the first and second cam surfaces so as to cause terminal ends of the pins of the first staple to translate in the transverse direction.

BRIEF DESCRIPTION OF THE DRAWINGS

The foregoing summary, as well as the following detailed description of example embodiments of the present disclosure, will be better understood when read in conjunction with the appended drawings. For the purposes of illustrating the example embodiments of the present disclosure, references to the drawings are made. It should be understood, however, that the application is not limited to the precise arrangements and instrumentalities shown. In the drawings:

FIG. 6A is a top plan view of an intervertebral implant including an implant body and a fixation assembly constructed in accordance with an alternative embodiment, having portions removed for the purposes of clarity, showing the fixation assembly in an extended position;

FIG. 6B is a front elevation view of the intervertebral implant as illustrated in FIG. 6A, shown disposed in an intervertebral space and in a retracted position;

FIG. 6C is a front elevation vie of the intervertebral implant as illustrated in FIG. 6B, having portions removed for the purposes of clarity;

FIG. 10A is a top plan view of an intervertebral implant including an implant body and a fixation assembly constructed in accordance with an alternative embodiment, having portions removed for the purposes of clarity, showing the fixation assembly in a retracted position;

FIG. 10B is a front elevation view of the intervertebral implant illustrated in FIG. 10A, having portions removed for the purposes of clarity, shown in an intervertebral space, and showing the fixation assembly in a retracted position;

FIG. 10C is a front elevation view of the intervertebral implant as illustrated in FIG. 10B, but showing the fixation assembly in an extended position;

FIG. 11A is a top plan view of an intervertebral implant including an implant body and a fixation assembly constructed in accordance with an alternative embodiment, having portions removed for the purposes of clarity, showing the fixation assembly in a retracted position;

FIG. 11B is a front elevation view of the intervertebral implant illustrated in FIG. 11A, having portions removed for the purposes of clarity, shown in an intervertebral space, and showing the fixation assembly in a retracted position;

FIG. 11C is a front elevation view of the intervertebral implant as illustrated in FIG. 11B, but showing the fixation assembly in an extended position;

FIG. 11D is a front elevation view of the intervertebral implant illustrated in FIG. 11B, showing the intervertebral implant in an as-assembled position;

FIG. 11E is a front elevation view of the intervertebral implant illustrated in FIG. 11B, showing the intervertebral implant in an as-supplied position;

FIG. 11F is a top plan view of the intervertebral implant as illustrated in FIG. 11E;

FIG. 12A is a top plan view of an intervertebral implant including an implant body and a fixation assembly constructed in accordance with an alternative embodiment, having portions removed for the purposes of clarity, showing the fixation assembly in a retracted position;

FIG. 12B is a front elevation view of the intervertebral implant as illustrated in FIG. 12A, having portions removed for the purposes of clarity, shown in an intervertebral space;

FIG. 12C is a front elevation view of the intervertebral implant as illustrated in FIG. 12B, but showing the fixation assembly in an extended position;

DETAILED DESCRIPTION

Figure 1A:
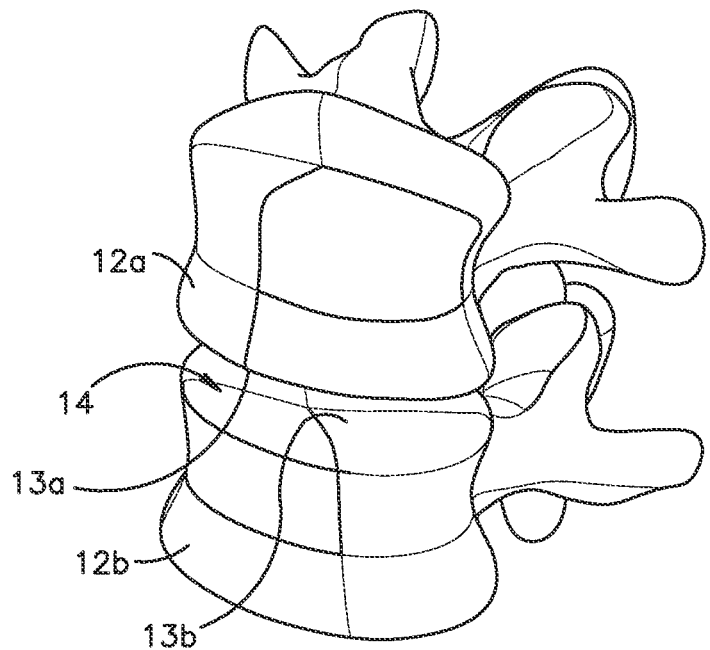
FIG. 1A is a perspective view of a pair of vertebral bodies separated by an intervertebral space.
Figure 1B:
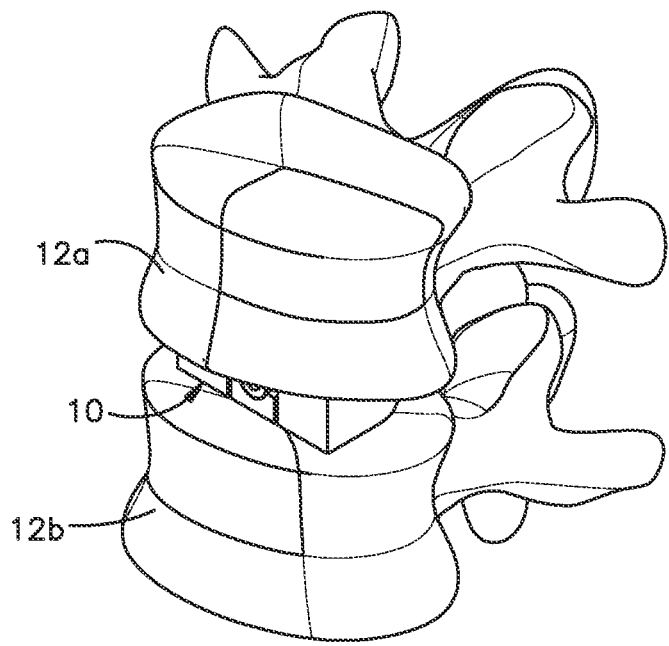
FIG. 1B is a perspective view of the vertebral bodies illustrated in FIG. 1, and an intervertebral implant inserted into the intervertebral space between the two vertebral bodies.

Referring to FIGS. 1A-B, a first superior vertebral body 12a defines a superior vertebral endplate 13a of an intervertebral space 14, and an adjacent second inferior vertebral body 12b defines an inferior vertebral endplate 13b of the intervertebral space 14. Thus, the intervertebral space 14 is disposed between the vertebral bodies 12a-b. The vertebral bodies 12a-b can be anatomically adjacent vertebral bodies, or can remain after a discectomy has been performed that removed a vertebral body from a location between the vertebral bodies 12a-b. As illustrated, the intervertebral space 14 is illustrated after a discectomy, whereby the disc material has been removed to prepare the intervertebral space 14 to receive an orthopedic implant, such as the intervertebral implant 10 illustrated in FIG. 2. Thus, the implant 10 is configured to be inserted into the intervertebral space 14, and achieve restoration of height while maintaining mobility. The intervertebral space 14 can be disposed anywhere along the spine as desired. As will be appreciated from the description below, the implant 10 can be sized as desired so as to be implantable in an intervertebral disc space in any region of the spine, including the lumbar region, thoracic region, cervical region, sacral region, and coccygeal region.

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof. The words, "anterior", "posterior," "superior," "inferior," "medial," "lateral," and related words and/or phrases designate preferred positions and orientations in the human body to which reference is made and are not meant to be limiting. The terminology includes the above-listed words, derivatives thereof and words of similar import.

The implant 10 and various components of the implant 10 are described herein extending horizontally along a longitudinal direction L and a lateral direction A, and vertically along a transverse direction T. Unless otherwise specified herein, the terms "lateral," "longitudinal," and "transverse" are used to describe the orthogonal directional components of various components. The lateral direction A and longitudinal direction L are angularly offset, for instance substantially orthogonal, with respect to each other and with respect to the transverse direction T. It should be appreciated that while the longitudinal and lateral directions are illustrated as extending along a horizontal plane, and that the transverse direction is illustrated as extending along a vertical plane, the planes that encompass the various directions may differ during use. For instance, when the implant 10 is implanted into an intervertebral space, such as the intervertebral space 14, the transverse direction T extends generally along the superior-inferior (or cranial-caudal) direction, while the plane defined by the longitudinal direction L and lateral direction A lie generally in the anatomical plane defined by the anterior-posterior direction, and the medial-lateral direction, respectively. Accordingly, the directional terms "vertical" and "horizontal" are used to describe the implant 10 and its components as illustrated merely for the purposes of clarity and illustration.

Figure 2A:
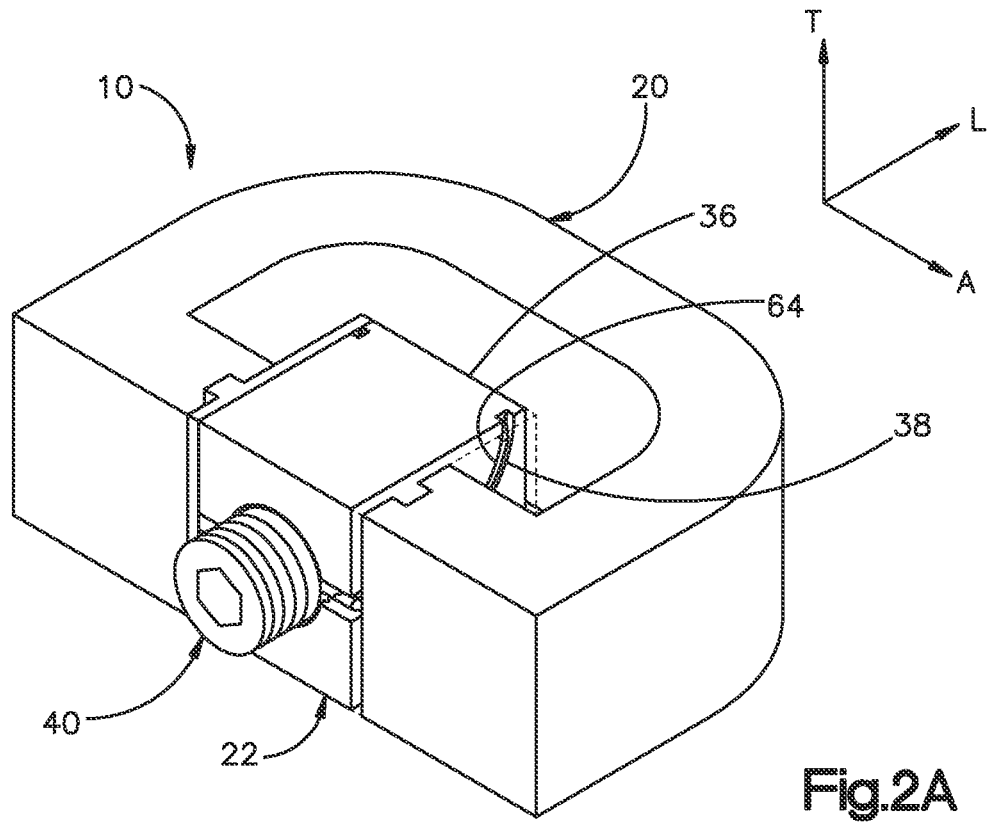
FIG. 2A is a perspective view of an intervertebral implant including an implant body and a fixation assembly connected to the intervertebral implant, showing the fixation assembly in accordance with one embodiment in a retracted position.
Figure 2B:
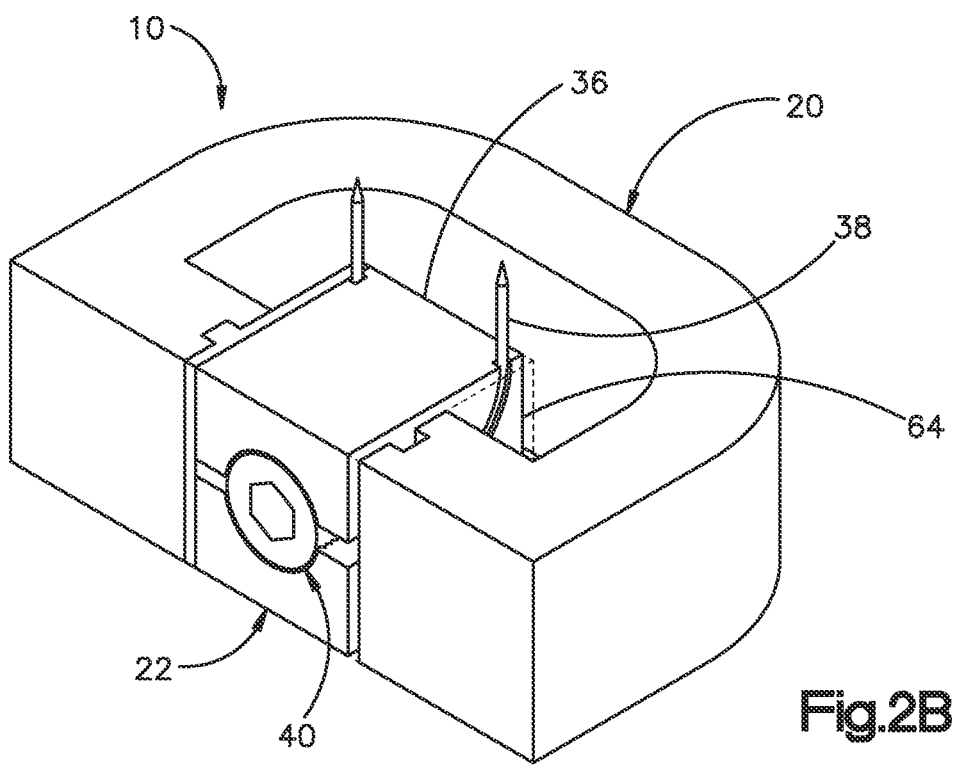
FIG. 2B is a perspective view of the intervertebral implant as illustrated in FIG. 2A, showing the fixation assembly in an extended position.
Figure 2C:
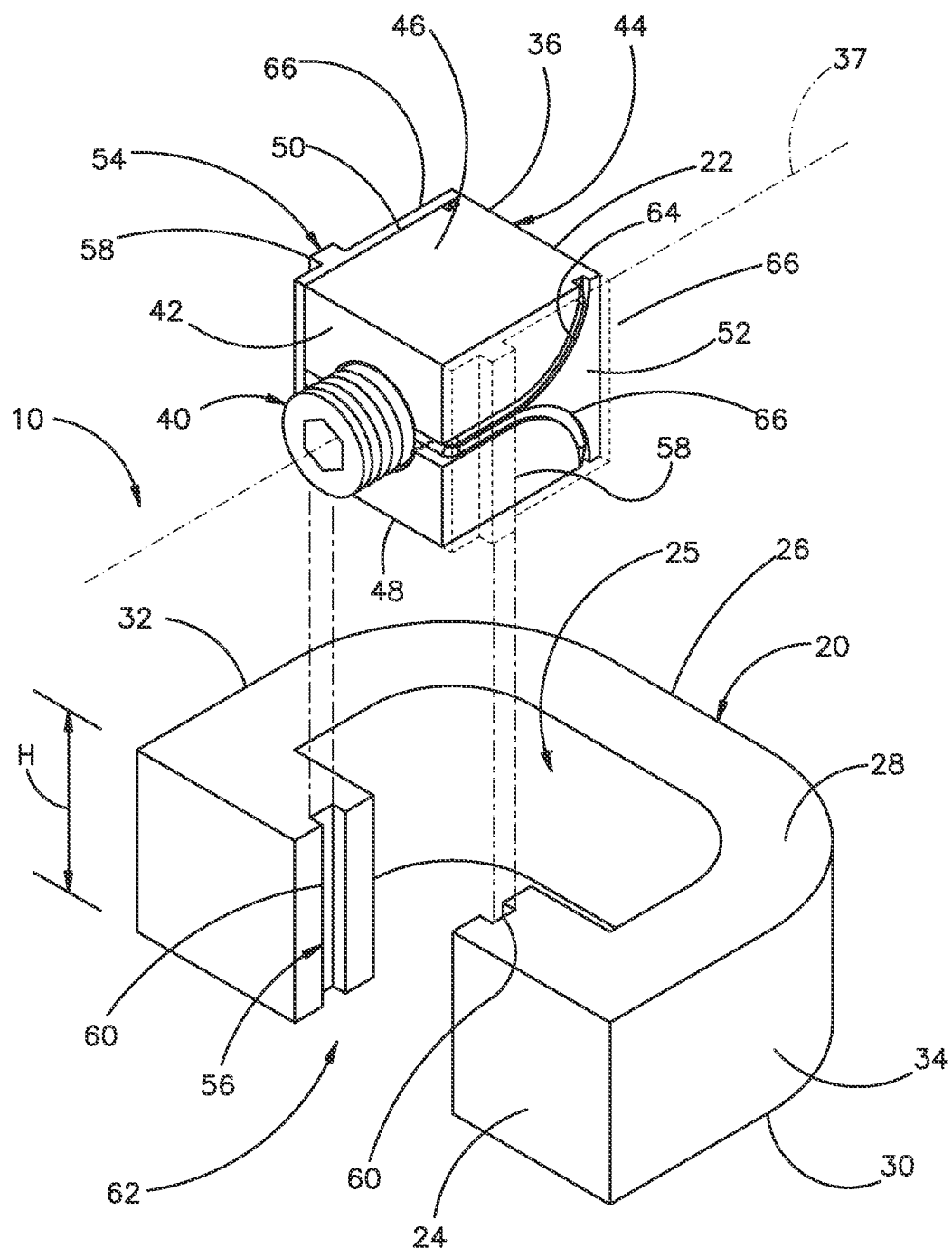
FIG. 2C is an exploded assembly view of the intervertebral implant illustrated in FIG. 2A, showing the connection of the fixation assembly to the implant body.

Referring now to FIGS. 2A-C, the intervertebral implant 10 includes an implant body 20 and a fixation assembly 22 configured to secure the implant body 20 to the first and second vertebral bodies 12a and 12b in the intervertebral space 14. The implant 10 and components thereof can be formed from any of a variety of biocompatible materials, such as cobalt chromium molybdenum (CoCrMo), titanium and titanium alloys, stainless steel, ceramics, or polymers such as polyetheretherketone (PEEK), ultra-high molecular weight polyethylenes (UHMWPE) or polysulfones (PSU), bioresorbable materials, and bonegraft (for example allograft and xenograft). A coating may be added or applied to the implant 10 to improve physical or chemical properties. The coatings may help to ensure bony in or on growth or medication. Examples of coatings include plasma-sprayed titanium coating or hydroxyapatite.

The implant body 20 defines a front end 24 and a longitudinally opposed rear end 26, a top end 28 and a transversely opposed bottom end 30, and opposed lateral sides 32 and 34. The top and bottom ends 28 and 30 can be configured to face the corresponding vertebral endplates 13a and 13b of the superior and inferior vertebral bodies 12a and 12b, respectively. In some embodiments, the top and bottom ends 28 and 30 can be configured to abut the corresponding vertebral endplates 13a and 13b. The implant 10 can be inserted into the intervertebral space 14 along an insertion direction which can be an anterior-posterior approach (for instance when the vertebral bodies 12a and 12b are cervical vertebral bodies) in an orientation such that the front longitudinal end 24 is anterior to the rear longitudinal end 26.

The implant body can be sized and shaped as desired, and is illustrated as substantially "D" shaped, such that the front end 24 extends substantially straight in the lateral direction A, and the lateral sides 32 and 34 curve toward each other in a rearward direction to the rear end 26. In accordance with the illustrated embodiment, the implant body 20 defines a substantially central "D" shaped central opening 25 that extends transversely into (through as illustrated) the implant body 20. The central opening 25 can receive any suitable bone growth promoting material, such as allograft and xenograft to promote bone growth with the vertebral bodies 12a-b after implantation of the implant 10 into the intervertebral space 14. The implant body 20 can be solid as illustrated, or can define perforations that extend into or through the implant body 20 that can, for instance, receive the bone growth promoting material.

The implant body 20 defines a transverse height H between the top and bottom ends 28 and 30. The height H can be substantially constant from the front end 24 to the rear end 26, or can be variable from the front end 24 to the rear end 26 so as to impart or restore a lordotic curvature to the vertebral bodies 12a and 12b. Thus, the height H can decrease in a rearward direction from the front end 24 toward the rear end 26, or can increase in the rearward direction. Furthermore, the height H can be constant or variable between the lateral sides 32 and 34 as desired. In this regard the top and bottom ends 28 and 30 can be substantially planar, or can be curved, undulated, or otherwise shaped as desired so as to correspond to the vertebral endplates 13a and 13b. A kit of implants 10 can also be provided, each having a plurality of implant bodies 20 of different shapes or sizes. For instance, the kit can include a plurality of implant bodies 20 of different heights H, such that at least one of the implant bodies 20 in the kit can correspond with the corresponding different height of intervertebral spaces along the vertebral column of a given patient, or of an intervertebral space of different patients.

The fixation assembly 22 includes a fixation housing 36 that is configured to be mounted or otherwise connected to the implant body 20. The fixation housing 36 supports, either directly or indirectly, at least one bone or vertebral fixation member 38 and at least one actuator 40 that is configured to iterate the fixation assembly 22, and particular the at least one fixation member 38, between a retracted position illustrated in FIG. 2A and an extended position illustrated in FIG. 2B so as to fix the fixation assembly 22 and thus the implant 10 to the vertebral bodies 12a and 12b. The fixation housing 36 defines a front end 42 and a longitudinally opposed rear end 44, a top end 46 and a transversely opposed bottom end 48, and opposed lateral side 50 and 52. The top and bottom ends 46 and 48 can be configured to face the corresponding vertebral endplates 13a and 13b of the superior and inferior vertebral bodies 12a and 12b, respectively. In some embodiments, the top and bottom ends 46 and 48 can be configured to abut the corresponding vertebral endplates 13a and 13b. In accordance with the illustrated embodiment, the front end 42 defines a proximal end of the fixation housing 36, and the rear end 44 defines a distal end of the fixation housing 36 that is spaced from the proximal end in the insertion direction along a central longitudinal axis 37.

The fixation housing 36 and the implant body 20 include respective complementary engagement members 54 and 56 that can be configured as desired to mount or otherwise connect the fixation housing 36 to the implant body 20. In accordance with the illustrated embodiment, the engagement member 54 of the fixation assembly 22 is configured as a transversely elongate rail 58 that projects laterally out from the sides 50 and 52 of the fixation housing 36. The rails 58 can terminate above the bottom end 48 of the fixation housing 36. In accordance with the illustrated embodiment, the complementary engagement member 56 of the implant body 20 is configured as a pair of transversely elongate slots 60 sized to receive the rails 58. The slot 60 can terminate above the bottom end 30 of the implant body 20. The slots 60 are disposed on opposed sides of a pocket 62 that is defined by the implant body 20 and sized to receive the fixation housing 36.

Accordingly, the fixation assembly 22 can be can be connected to the implant body 20 by inserting the fixation housing 36 into the pocket 62 of the implant body 20 such that the rails 58 are received in the slots 60. The fixation housing 36 can define a longitudinal length greater than the front end 24 of the implant body 20, such that the fixation housing 36 extends longitudinally into the central opening 25. The rails 58 and slots 60 can be sized such that the top and bottom ends 46 and 48 of the fixation housing 36 are substantially aligned or flush with the top and bottom ends 28 and 30 of the implant body 20. Accordingly, the top and bottom ends 46 and 48 of the fixation housing 36, and the top and bottom ends 28 and 30 of the implant body 20, can be configured to abut the vertebral endplates 13a and 13b. Alternatively, part or all of the top and bottom ends 28 and 30 of the implant body 20 and/or the top and bottom ends 46 and 48 of the fixation housing can be recessed with respect to the vertebral endplates 13a and 13b. Whether the top ends 28 and 46 and bottom ends 30 and 48 abut or are recessed from the respective vertebral endplates 13a and 13b, they can face a direction having a transverse directional component, such that it can be said that the top ends 28 and 46 and bottom ends 30 and 48 face the vertebral bodies 12a and 12b and thus define vertebral body facing surfaces. As described above, the engagement members 54 and 56 can be configured as desired to facilitation the connection of the fixation assembly 20 to the implant body 20. For instance, the fixation assembly 22 can be integral with the implant body 20.

Figure 2D:
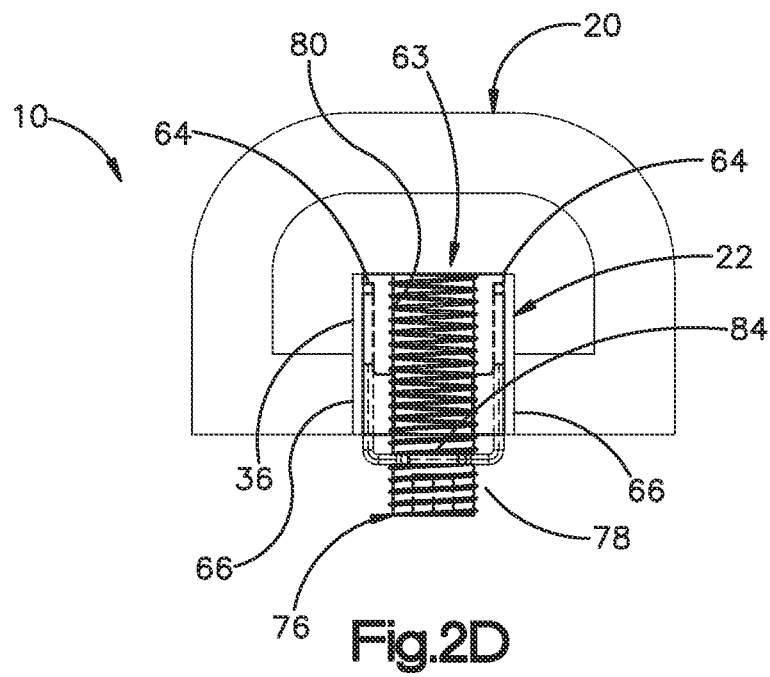
FIG. 2D is a top plan view of the intervertebral implant illustrated in FIG. 2A having portions removed for the purposes of clarity.
Figure 2E:
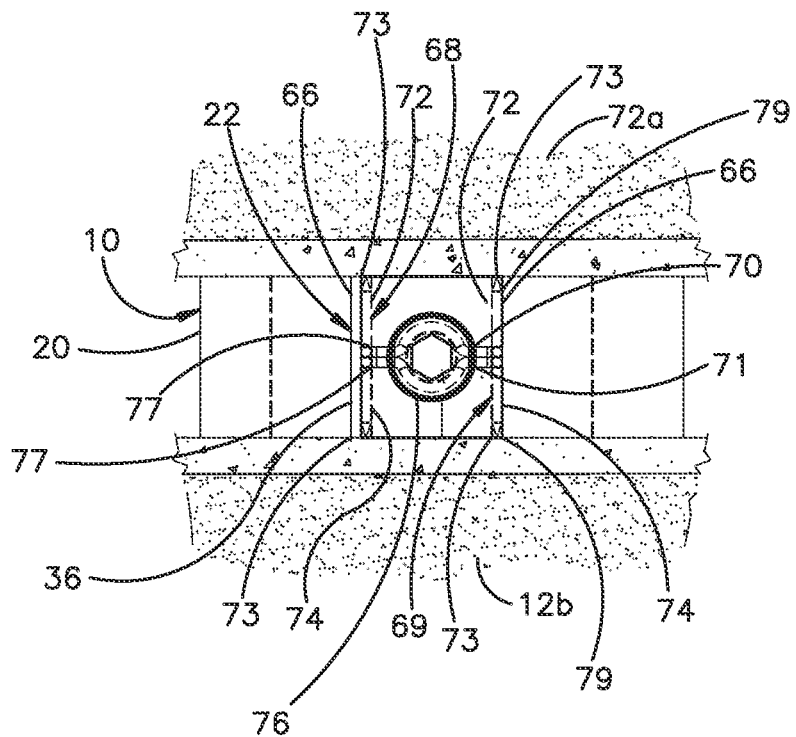
FIG. 2E is a front elevation view of the intervertebral implant as illustrated in FIG. 2A, having portions removed for the purposes of clarity, shown in an intervertebral space.
Figure 2F:
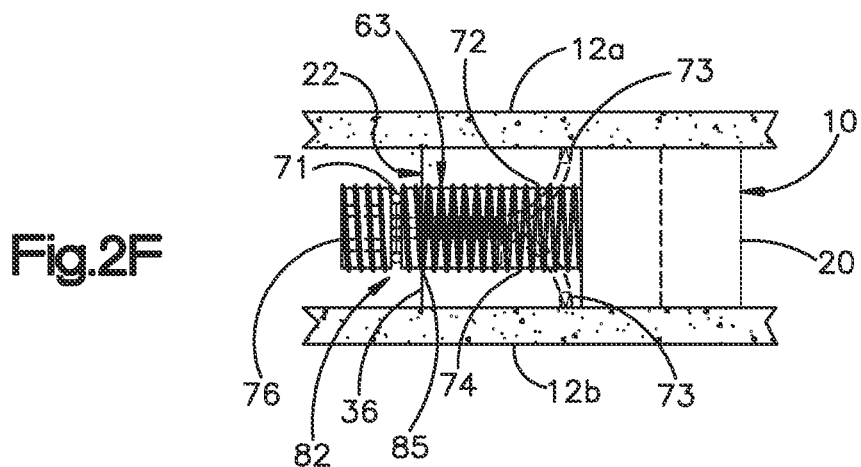
FIG. 2F is a side view of the intervertebral implant as illustrated in FIG. 2E, having portions removed for the purposes of clarity.
Figure 2G:
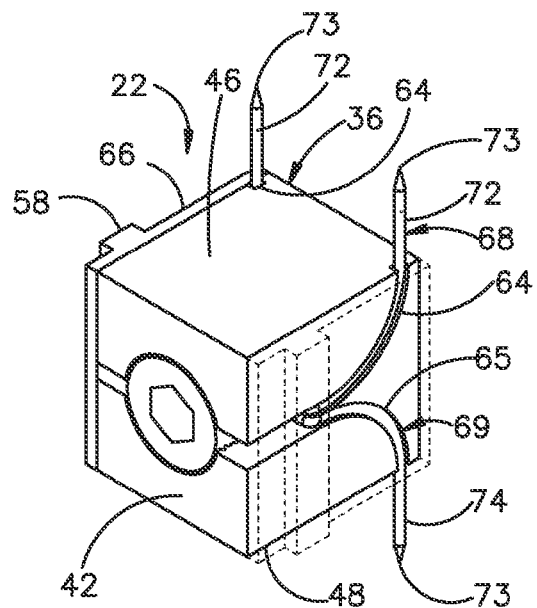
FIG. 2G is a perspective view of the fixation assembly as illustrated in FIG. 2B.
Figure 2H:
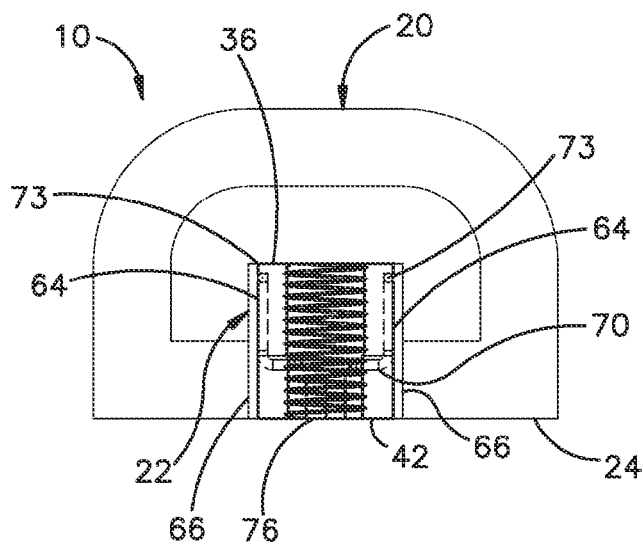
FIG. 2H is a top plan view of the intervertebral implant as illustrated in FIG. 2B, having portions removed for the purposes of clarity.
Figure 2I:
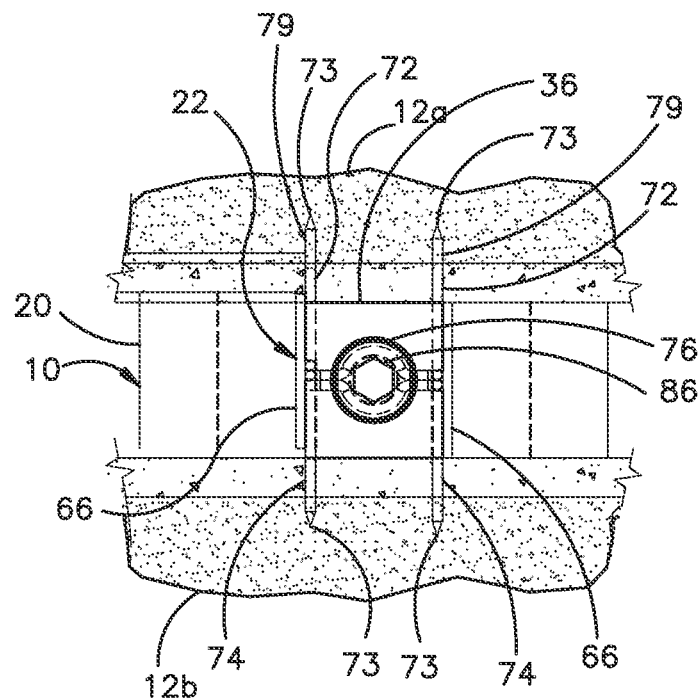
FIG. 2I is a front elevation view of the intervertebral implant as illustrated in FIG. 2B, having portions removed for the purposes of clarity, shown in an intervertebral space.
Figure 2J:
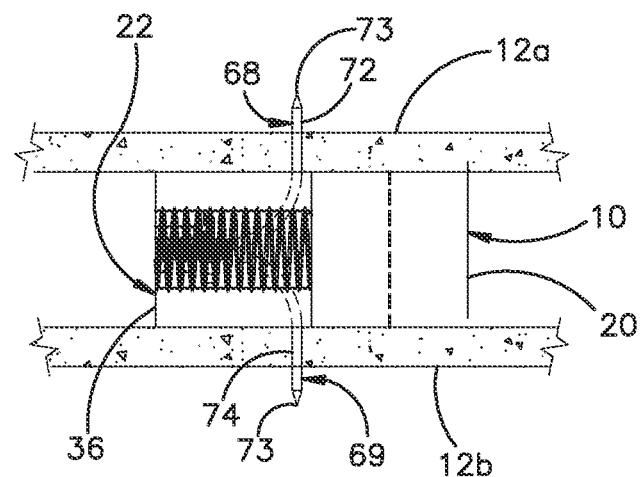
FIG. 2J is a side view of the intervertebral implant as illustrated in FIG. 2I, having portions removed for the purposes of clarity.

Referring also to FIGS. 2D-F, the fixation assembly 22 includes at least one aperture 63 defined by the fixation housing 36 that receives the actuator 40 and at least one channel that receives the at least one fixation member 38. In accordance with the illustrated embodiment, the fixation housing 36 defines a first pair of laterally spaced superior channels 64 and a second pair of laterally spaced inferior channels 65 that can be vertically aligned with the superior channels 64. The channels 64 and 65 can extend in any direction as desired, and extend in a direction having both longitudinal and transverse directional components in accordance with the illustrated embodiment. For instance the superior channels 64 extend longitudinally and transversely upwards so as to define a first proximal end that extends from the proximal end 42 of the fixation housing 36 to a second distal end that extends to the top end 46. The inferior channels 65 extend longitudinally and transversely down so as to define a first proximal end that extends from the proximal end 42 of the fixation housing 36 to the distal end that extends to the bottom end 48. The distal ends of the channels 64 and 65 are thus transversely and longitudinally displaced with respect to the respective proximal ends of the channels 64 and 65.

In accordance with the illustrated embodiment, the channels 64 and 65 extend laterally into the sides 50 and 52 of the fixation housing 36, though they can be alternatively positioned as desired. The fixation assembly 22 can include a pair of cover plates 66 that are attached to the sides 50 and 52 of the fixation housing 36 so as to laterally cover and laterally close the channels 64 and 65. Thus, the cover plates 66 can include the engagement rails 58 as described above.

The fixation member 38 can be provided as a first staple 68 that defines a proximal end 77 and an opposed distal or terminal end 79 that, in turn, defines a corresponding tip 73 that is configured to be inserted into a corresponding vertebral body (e.g., through the endplate) so as to fix the fixation assembly 22 and thus the implant 10 to the vertebral body. The staple 68 includes a bass in the form of a crossbar 70 at the proximal end 77 and at least a first pair of laterally spaced pins 72 that extend out from the crossbar 70 at any location, such as at opposed outer ends of the crossbar 70 as illustrated. The implant 10 can include a second fixation member provided as a second staple 69 can further include a second pair of laterally spaced pins 74 that extend out from a second crossbar 71 at any location, such as at opposed outer ends of the crossbar 71 as illustrated.

The pins 72 and 74 are attached to the respective crossbars 70 and 75 at their proximal ends, and define the tips 73 at their distal ends. When the staples 68 and 69 are in the recessed position, the pins 72 and 74 can be entirely recessed in the fixation housing 36 such that the tips 73 do not extend out from the fixation housing 36. The tips 73 of the first and second pairs of pins 72 and 74 can extend into the vertebral bodies 12a and 12b when the fixation member 38 is in the extended position. Thus the implant 10 can include a pair of fixation members that define respective pairs of pins 72 and 74, the first pair of pins 72 defining a tip 73 at its distal or terminal end that is configured to extend into the first vertebral body 12a in the extended position, and the second pair of pins 72 defining a tip that is configured to extend into the second vertebral body 12b in the extended position.

In accordance with the illustrated embodiment, the first pair of pins 72 extends superiorly and longitudinally distally from the crossbar 70 in the superior channels 64, and the second pair of pins 74 extends inferiorly and longitudinally distally from the crossbar 71 in the inferior channels 65. It should be appreciated, however, that the first and second pairs of pins 72 and 74 can extend from the same crossbar if desired. The channels 64 and 65 can curve along their length along a constant radius such that the pins 72 and 74 can be made from any suitable rigid material, or the channels 64 and 65 can define different curvatures along their length, such that the pins 72 and 74 can be made of any suitable flexible material. For instance the pins 72 and 74 can be made from titanium or nitinol (nickel titanium). As will be described in more detail below, the pins 72 and 74 are movable within the channels 64 and 65 from the retracted position to the extended position whereby the distal ends of the pins 72 and 74 extend out from the fixation housing 36 and into the corresponding vertebral bodies 12a and 12b when the implant 10 is disposed in the intervertebral space 14. The distal ends of the pins 72 and 74 can extend out from the fixation housing 36 substantially in the transverse direction T.

With continuing reference to FIGS. 2A-F, the actuator 40 is configured to iterate the fixation member 38 from the retracted position to the extended position. In accordance with the illustrated embodiment, the actuator 40 can be provided as a screw 76 that defines external threads 78 along part or all of the length of a screw shaft 89 that engages corresponding internal threads 80 of the aperture 63. Accordingly, the screw 76 can translate distally in the aperture 63 and thus the fixation housing 36 as the screw 76 is rotated in the aperture 63 relative to the fixation housing 36. During operation, the screw 76 can translate along a direction that has a longitudinal directional component (e.g., distally) from a disengaged position to an engaged position. When the screw 76 is in the disengaged position, the fixation member 38 is in the retracted position. When the screw 76 moves to the engaged position, the screw 76 moves the fixation member 38 to the extended position.

Referring also to FIGS. 2G-J, the screw 76 defines a first engagement member illustrated as a groove 82 that can extend circumferentially or about an arc about the screw 76. The crossbars 70 and 71 define respective apertures, which can be cylindrical, that extends longitudinally through the crossbars 70 and 71, such that the crossbars 70 and 71 define a respective collars 84 and 85 that are sized to be inserted into the groove 82. The collars 84 and 85 can be circumferentially sized slightly greater than the groove 82 such that the screw 76 is rotatable with respect to the collars. The longitudinal dimension of the collars 84 and 85 can be substantially equal to that of the groove 82 such that the collars 84 and 85, and thus the staples 68 and 69, are substantially longitudinally fixed to the screw 76 such that the staples 68 and 69 translate as the screw 76 translates in the aperture 63. Thus, the pins 72 and 74 translate distally in the respective channels 64 and 65 to the extended position as the screw 76 translates, whereby the distal ends of the pins 72 and 74, and thus the tips 73, extend transversely out from the fixation housing 36 to a location transversely out from at least a portion of the implant body 20. The distal ends of the channels 64 and 65 can extend substantially transversely such that the portion of the pins 72 and 74 that extend out from the channels 64 and 65, including the tips 73, can be directed substantially in the transverse direction into the respective vertebral bodies 12a and 12b.

The screw 76 defines an engagement member illustrated as a socket 86 that extends longitudinally into the proximal end of the screw 76. The socket 86 is illustrated as a hexagonal in shape, though it could be shaped as any suitable polygonal shape, including a "plus" shape, a "dash" shape, or any alternative shape as desired. Because the socket 86 extends longitudinally into the screw 76, the socket 86 defines a depth that is substantially parallel to the insertion direction of the implant 10 into the intervertebral space 14. Accordingly, an anterior approach into the intervertebral space 14 can facilitate both insertion of the implant 10 into the intervertebral space and movement of the actuator 40 from the disengaged position to the engaged position, thereby correspondingly causing the fixation member 38 to move from the retracted position to the extended position.

Thus, an actuator tool, such as a hex drive, can be inserted into the socket 86 and rotated, either manually or automatically so as to cause the screw 76 to rotate and translate distally relative to the fixation housing 36. In accordance with the illustrated embodiment, the proximal end of the screw 76 extends longitudinally out to a location proximal of the front end 42 of the fixation housing 36 when the screw is in the disengaged position. As the screw 76 translates distally to the engaged position, the screw 76 translates distally until the screw 76 reaches the engaged position. For instance, the aperture 63 can terminate at a location that prevents further translation of the screw 76 once the screw 76 has reached the engaged position. In accordance with the illustrated embodiment, proximal end of the screw 76 is substantially flush with the front end 42 of the fixation housing when the screw 76 is in the engaged position. As the screw 76 translates distally, the fixation member 38 likewise translates distally, which causes the pins 72 and 74 to travel distally in their respective channels 64 and 65, thereby causing the tips 73 to initially protrude transversely from the upper and lower ends 46 and 48, respectively, of the fixation housing 36. As the screw 76 and pins 72 and 74 continue to translate distally, the tips 73 extend increasingly out from the fixation housing 36 until the screw 76 is in the engaged position, at which point the tips 73 of the pins 72 and 74 are fully extended out from the fixation housing 36 and into the vertebral bodies 12a and 12b.

If it is desired to retract the pins 72 and 74 so as to facilitate removal of the implant 10 from the intervertebral space 14, the screw 76 can be rotated relative to the fixation housing 36 in a second opposite direction, thereby causing the screw 76 to translate proximally from the engaged position to the disengaged position. As the screw 76 translates proximally, the fixation member 38 likewise translates proximally, thereby causing the tips of the pins 72 and 74 to retract toward the respective channels 64 and 65. When the screw 76 has been fully retracted such that the screw is in the disengaged position, the tips 73 of the pins 72 and 74 can be recessed with respect to the vertebral bodies 12a and 12b, and fully retracted in the respective channels 64 and 65, at which point the implant 10 can be removed from the intervertebral space 14.

While the implant has been described in accordance with one embodiment, it should be appreciated that the implant 10 can be constructed in accordance with any alternative embodiment as desired having at least one fixation member that is configured to move between a retracted position to an extended position as described above. A number of such alternative embodiments are described below, it being appreciated that the embodiments are described herein for the purposes of illustration, and that other alternative embodiments are contemplated beyond those explicitly described herein, for instance as defined by the appended claims.

Figure 3A:
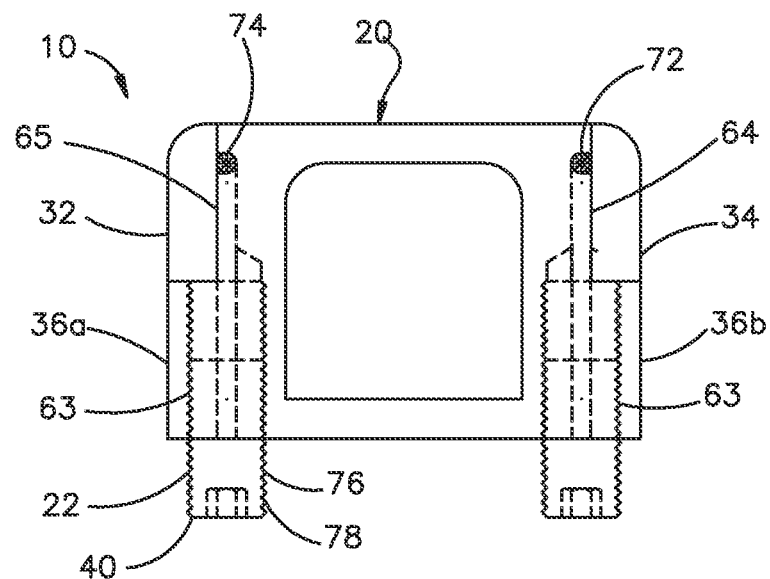
FIG. 3A is a top plan view of an intervertebral implant including an implant body and a fixation assembly constructed in accordance with an alternative embodiment, having portions removed for the purposes of clarity, showing the fixation assembly in a retracted position.
Figure 3B:
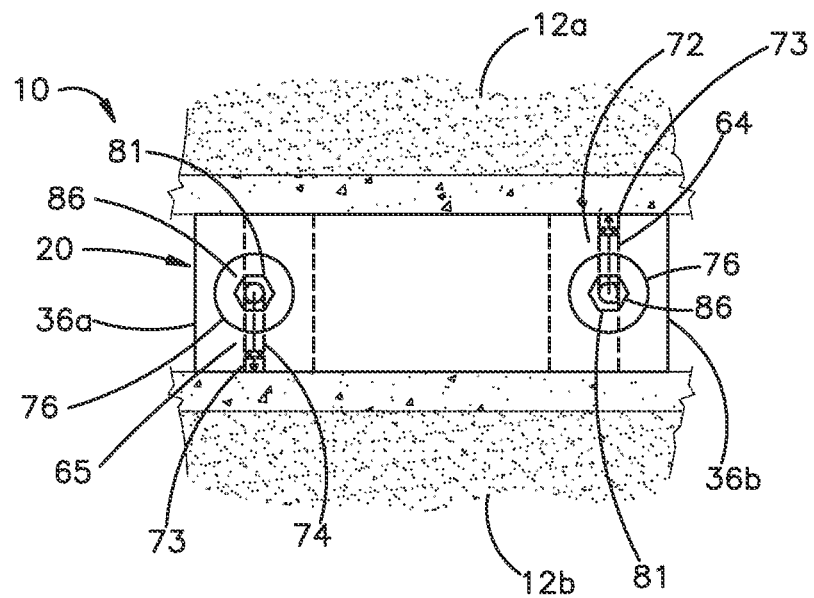
FIG. 3B is a front elevation view of the intervertebral implant as illustrated in FIG. 3A, having portions removed for the purposes of clarity, shown in an intervertebral space.
Figure 3C:
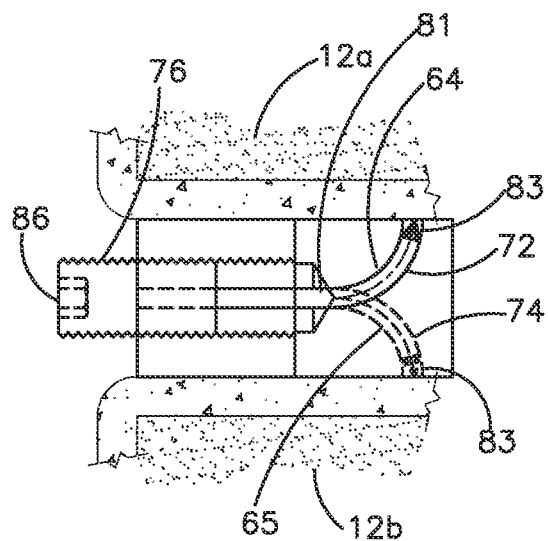
FIG. 3C is a side elevation view of the intervertebral implant as illustrated in FIG. 3B, having portions removed for the purposes of clarity.

For instance, referring to FIGS. 3A-C, the fixation assembly 22 of the implant 10 is illustrated in accordance with an alternative embodiment, whereby the fixation housing 36 includes a pair of laterally spaced fixation housing segments 36a and 36b that are connected to the lateral sides 32 and 34 of the implant body 20. Each housing segment 36a and 36b defines an aperture 63 that receives an actuator 40 illustrated as a screw 76 in the manner described above. The superior channel 64 extends centrally from one of the apertures 63 in the housing segment 36b, and the inferior channel 65 extends centrally from the other aperture 63 in the housing segment 36a. Each of the screws 76 can define a bore 81 that extends centrally into their distal ends, such that the proximal ends of at least a first fixation member illustrated as a first pin 72 extends into the central bore 81 of the screw 76 disposed in the housing segment 36a. The first pin 72 further extends into the superior channel 64. The proximal ends of at least a second fixation member illustrated as a pin 74 extends into the central bore 81 of the screw 76 disposed in the housing segment 36b, such that the second pin further extends into the inferior channel 64.

Figure 3D:
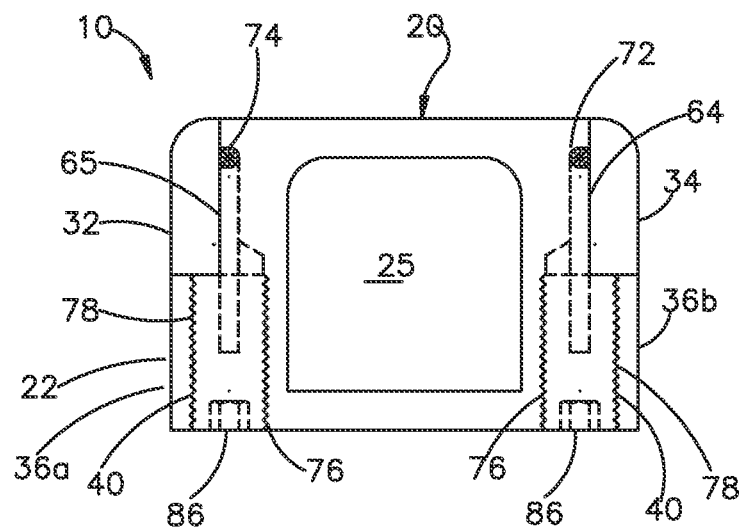
FIG. 3D is a top plan view of the intervertebral implant illustrated in FIG. 3A, but showing the fixation assembly in an extended position.
Figure 3E:
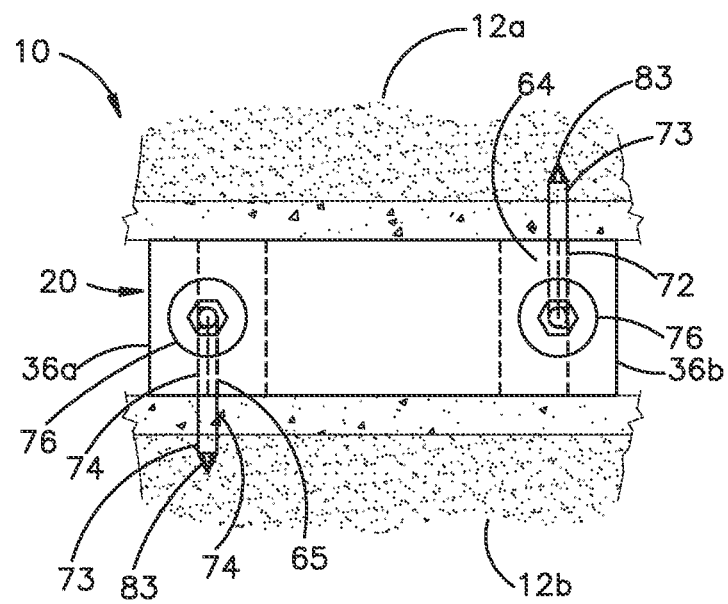
FIG. 3E is a front elevation view of the intervertebral implant as illustrated in FIG. 3D, having portions removed for the purposes of clarity, shown in an intervertebral space.
Figure 3F:
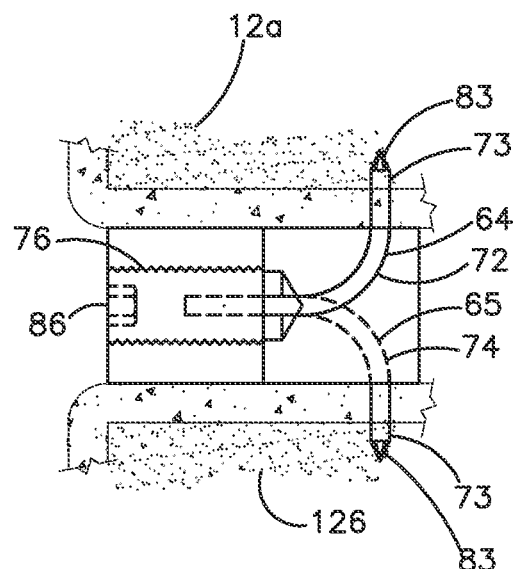
FIG. 3F is a side elevation view of the intervertebral implant as illustrated in FIG. 3D, having portions removed for the purposes of clarity.

Referring also to FIGS. 3D-F, the proximal ends of the pins 72 and 74 are rotatably coupled to the respective screws inside the bore 81, and can be attached to the screws 76 via adhesive or weldments, or can alternatively be integrally connected to the screws 76. Thus, the pins 72 and 74 are coupled to the respective screws 76 with respect to both translation and rotation, such that the pins 72 and 74 both rotate and translate along with the respective screws 76 to which they are connected. The pins 72 and 74 extend into the respective channels 64 and 65, which extend superiorly and inferiorly, respectively, and longitudinally distally as described above. Accordingly, the screws 76 translate as they rotate in the housing 36 in the manner described above, which causes the pins 72 and 74 to rotate as they travel distally in the respective channels 64 and 65. The tips 73 therefore also rotate as they translate out from the fixation housing 36. The pins 72 and 74 can each include a cutting bit, for instance cutting flutes 83, at their tips 73 so as to facilitate cutting into the vertebral bodies 12a and 12b as the pins 72 rotate and translate from their retracted positions to their extended positions.

Figure 3G:
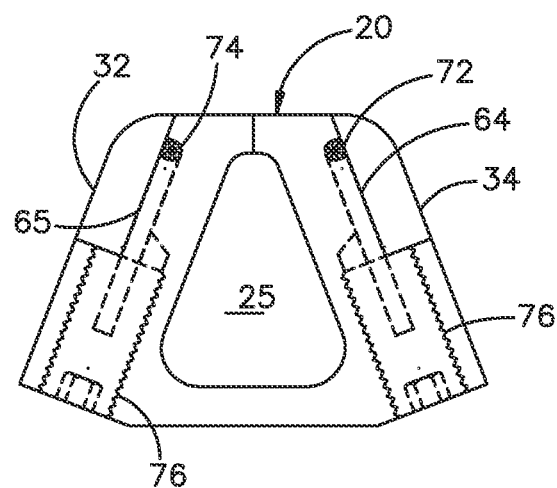
FIG. 3G is a top plan view of an intervertebral implant similar to the intervertebral implant as illustrated in FIG. 3D, but constructed in accordance with an alternative embodiment.

The screws 76, channels 64 and 65, and pins 72 and 74, can extend substantially parallel to each other (longitudinally as illustrated in FIGS. 3A-F), or can be angularly offset with respect to each other. For instance, the screws 76 and the channels 64 and 65, and thus the pins 72 and 74, can converge toward each other along a direction from their proximal ends to their distal ends as illustrated in FIG. 3G. Alternatively still, the channels 64 and 65 can diverge away from each other along a direction from their proximal ends to their distal ends.

Alternatively still, the implant 10 can include a pair of screws 76 at each lateral side 32 and 34. For instance, each side 32 and 34 can include a superior screw 76 coupled to a superior pin in the manner described above, and an inferior screw 76 located inferior with respect to the superior screw and coupled to an inferior pin in the manner described above, such that each lateral side of the implant body 20 can be fixed to both the superior vertebral body 12*a* and the inferior vertebral body 12*b*.

Figure 4A:
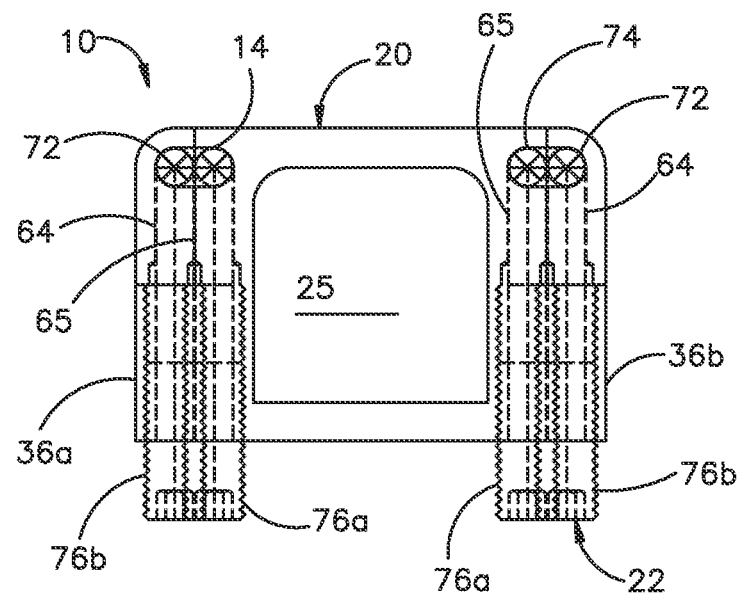
FIG. 4A is a top plan view of an intervertebral implant including an implant body and a fixation assembly constructed in accordance with an alternative embodiment, having portions removed for the purposes of clarity, showing the fixation assembly in a retracted position.
Figure 4B:
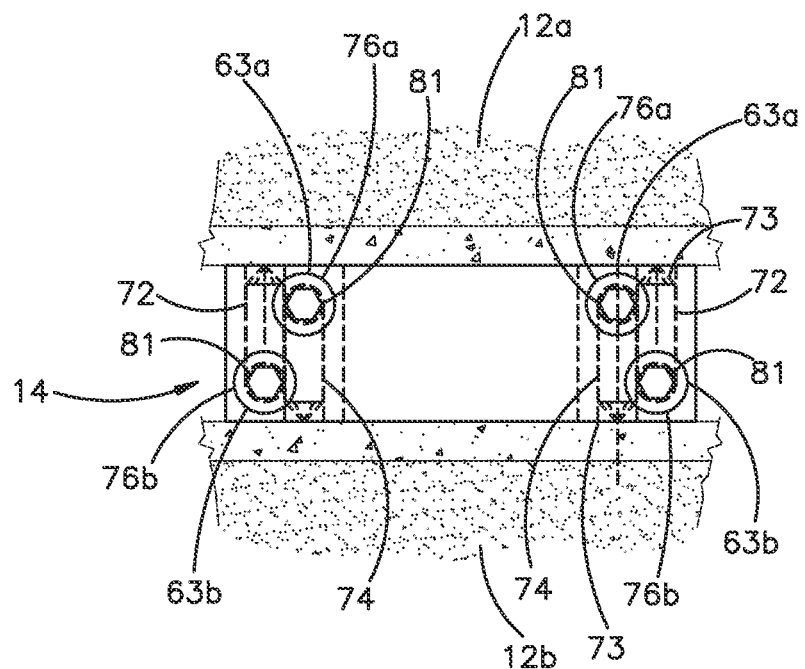
FIG. 4B is a front elevation view of the intervertebral implant as illustrated in FIG. 4A, having portions removed for the purposes of clarity, shown in an intervertebral space.
Figure 4C:
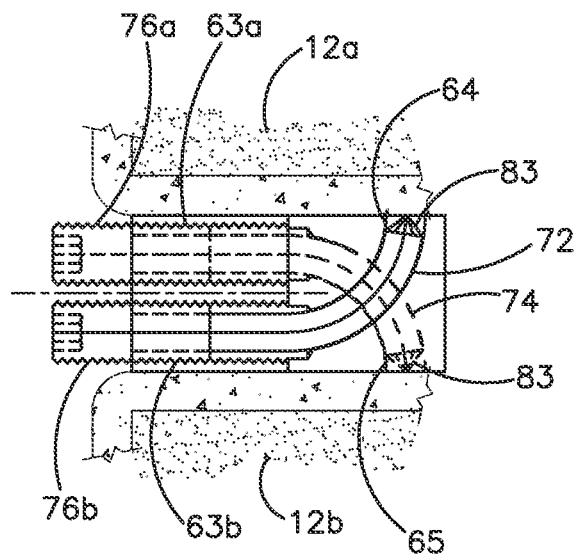
FIG. 4C is a side elevation view of the intervertebral implant as illustrated in FIG. 4B, having portions removed for the purposes of clarity.

Referring now to FIGS. 4A-C, the fixation assembly 22 of the implant 10 is illustrated in accordance with an alternative embodiment, whereby the laterally spaced fixation housing segments 36*a* and 36*b* each include a superior aperture 63*a* and an inferior aperture 63*b* that each receive an actuator 40 illustrated as a superior screw 76*a* and an inferior screw 76*b* in the manner described above. The superior aperture 63*a* and the inferior aperture 63*b* can be laterally displaced from each other by a distance at least equal to the thickness of the channels 64 and 65. Accordingly, the superior channel 64 can extend from the inferior aperture 63*b* and the inferior channel 65 can extend from the superior aperture 63*a*, such that the channels 64 and 65 in each housing segment 36*a* and 36*b* cross over each other and can be longitudinally and transversely aligned without interfering with each other.

The superior channels 64 extend centrally from the inferior apertures 63 in the housing segments 36*a* and 36*b*, and the inferior channels 65 extend centrally from the apertures 63 in the housing segments 36*a* and 36*b*. Each of the screws 76*a* and 76*b* can define a bore 81 that extends centrally into their distal ends. The proximal ends of at least a first fixation member 38 such as a pair of first fixation members illustrated as a pair of first pins 72 extends into the central bore 81 of the corresponding pair of the inferior screws 76*b* that are disposed in the inferior apertures 63*b* and aligned with the superior channels 64. The first pins 72 further extend into the superior channels 64 from the inferior screws 76*b*. The proximal ends of at least a second fixation member such as a pair of second fixation members illustrated as a pair of second pins 74 extends into the central bore 81 of the corresponding pair of superior screws 76*a* that are disposed in the superior apertures 63*a* and aligned with the inferior channels 65. The second pins 74 further extend into the inferior channels 65 from the superior screws 76*a*.

Figure 4D:
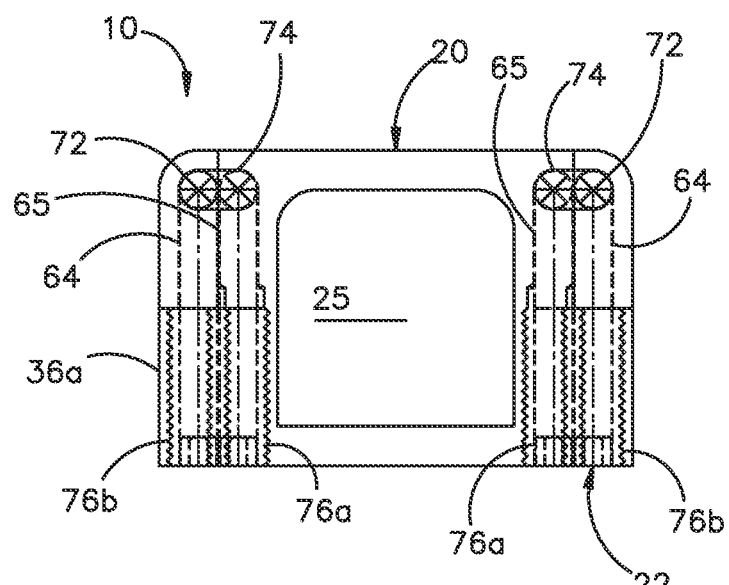
FIG. 4D is a top plan view of the intervertebral implant illustrated in FIG. 4A, but showing the fixation assembly in an extended position.
Figure 4E:
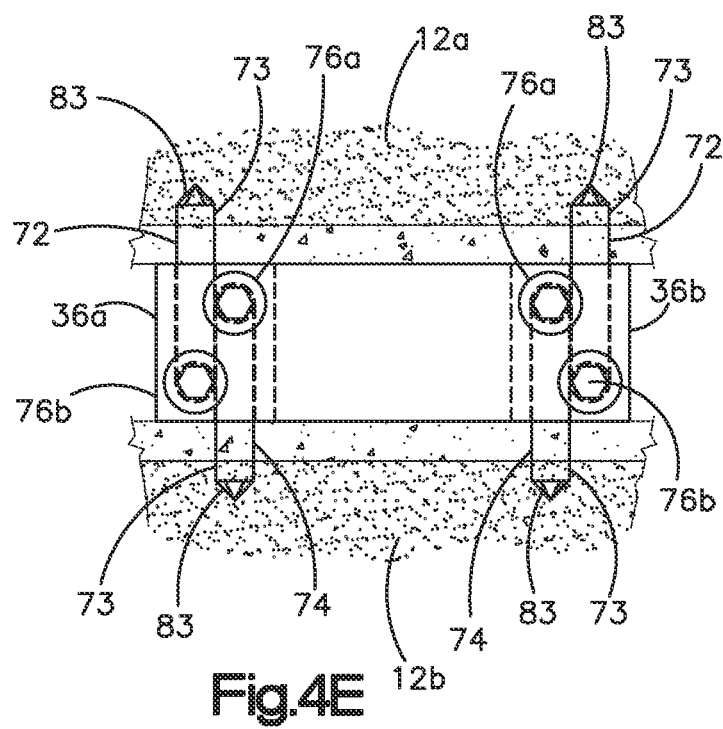
FIG. 4E is a front elevation view of the intervertebral implant as illustrated in FIG. 4D, having portions removed for the purposes of clarity, shown in an intervertebral space.
Figure 4F:
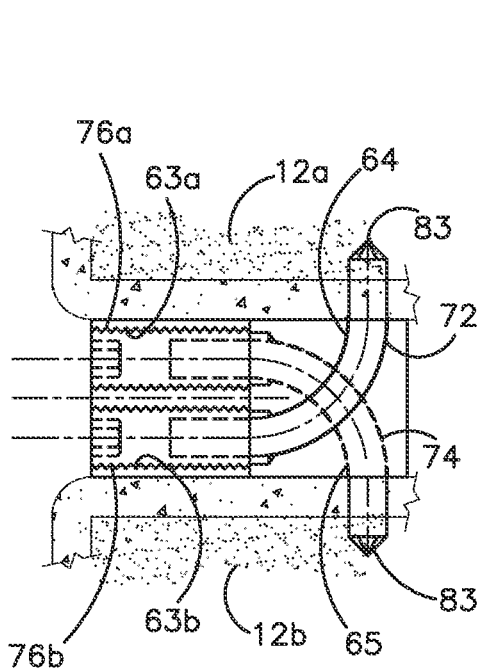
FIG. 4F is a side elevation view of the intervertebral implant as illustrated in FIG. 4D, having portions removed for the purposes of clarity.

Referring also to FIGS. 4D-F, the proximal ends of the pins 72 and 74 are rotatably coupled to the respective screws 76*a* and 76*b* inside the bore 81, and can be attached to the screws 76*a* and 76*b* via adhesive or weldments, or can alternatively be integrally connected to the screws 76*a* and 76*b*. Thus, the pins 72 and 74 are coupled to the respective screws 76*b* and 76*a* with respect to both translation and rotation, such that the pins 72 and 74 rotate and translate with the respective screws 76*b* and 76*a* to which they are connected. The pins 72 extend into the superior channels 64 from the inferior screws 76*b*, and the pins 74 extend into the inferior channels 65 from the superior screws 76*a*.

Both channels 64 and 65 extend from the respective apertures 63*b* and 63*a* in a direction having both longitudinal and transverse directional components. The proximal ends of the superior channels 64 are inferior with respect to the proximal ends of the inferior channels 65, and the distal ends of the superior channels 64 are superior with respect to the superior ends of the inferior channels 65. For instance, the distal ends of the superior channels 64 extend through the top end of the fixation housing 36 and/or implant body 20. The distal ends of the inferior channels 64 extend through the bottom end of the fixation housing 36 and/or implant body 20. During operation, the screws 76 translate as they rotate in the housing 36 in the manner described above, which causes the pins 72 and 74 to rotate as they travel distally in the respective channels 64 and 65. The tips 73 therefore also rotate as they translate out from the fixation housing 36. The pins 72 and 74 can each include a cutting bit, for instance cutting flutes 83, at their tips 73 so as to facilitate cutting into the vertebral bodies 12*a* and 12*b* as the pins 72 rotate and translate from their retracted positions to their extended positions. The pins 72 that are connected to the inferior screws 76*b* extend through the superior channels 64 such that the tips 73 extend transversely outward with respect to the fixation housing 36 and/or the implant body 20 along a direction having a transverse directional component into the superior vertebral body 12*a* when the implant 10 is disposed in the intervertebral space 14 and the pins 72 have been iterated to their extended position. The pins 74 that are connected to the superior screws 76*a* extend through the inferior channels 65 such that the tips 73 extend transversely outward with respect to the fixation housing 36 and/or the implant body 20 along a direction having a transverse directional component into the inferior vertebral body 12*b* when the implant 10 is disposed in the intervertebral space 14 and the pins 74 have been iterated to their extended position.

Figure 4G:
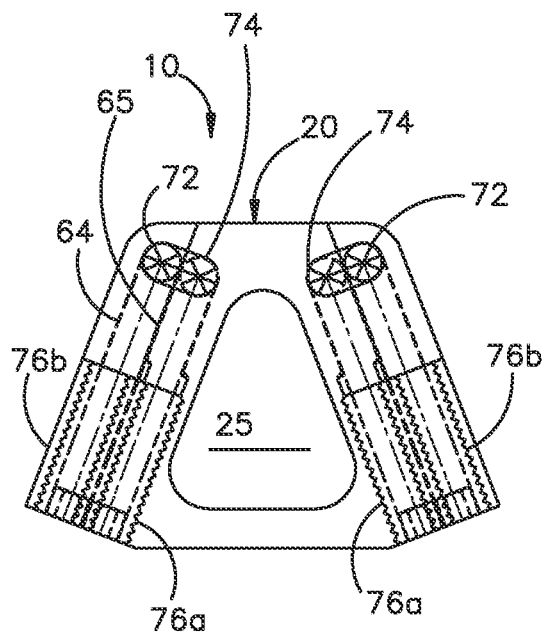
FIG. 4G is a top plan view of an intervertebral implant similar to the intervertebral implant as illustrated in FIG. 4D, but constructed in accordance with an alternative embodiment.
Figure 5A:
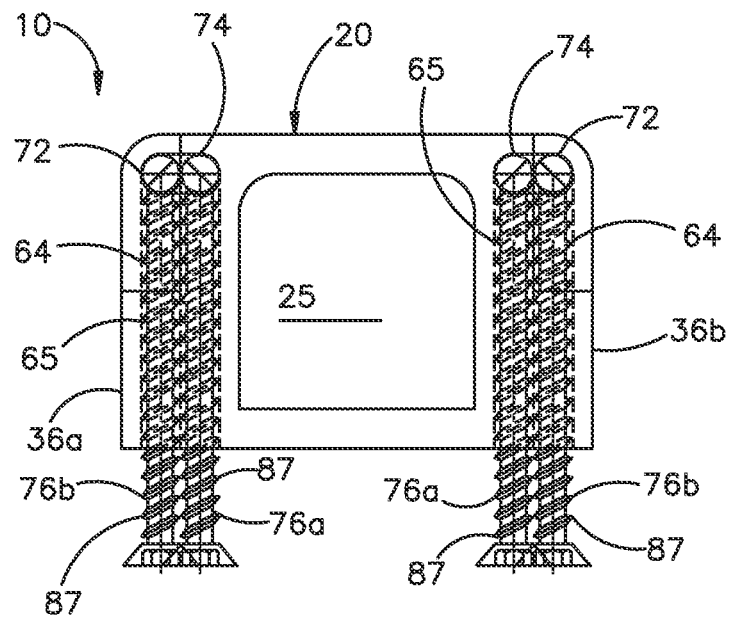
FIG. 5A is a top plan view of an intervertebral implant including an implant body and a fixation assembly constructed in accordance with an alternative embodiment, having portions removed for the purposes of clarity, showing the fixation assembly in a retracted position.
Figure 5B:
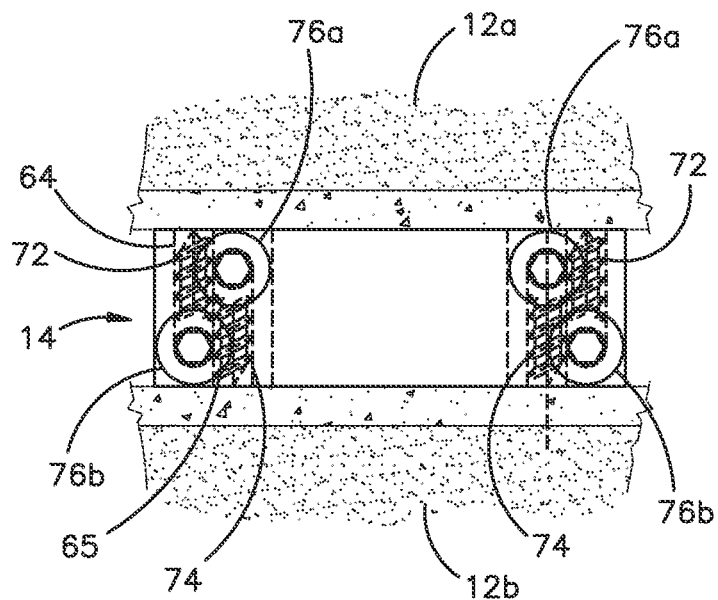
FIG. 5B is a front elevation view of the intervertebral implant as illustrated in FIG. 5A, having portions removed for the purposes of clarity, shown in an intervertebral space.
Figure 5C:
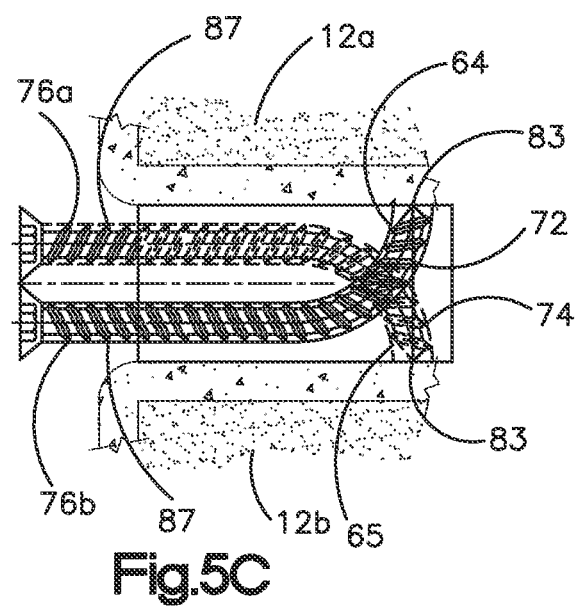
FIG. 5C is a side elevation view of the intervertebral implant as illustrated in FIG. 5B, having portions removed for the purposes of clarity.
Figure 5D:
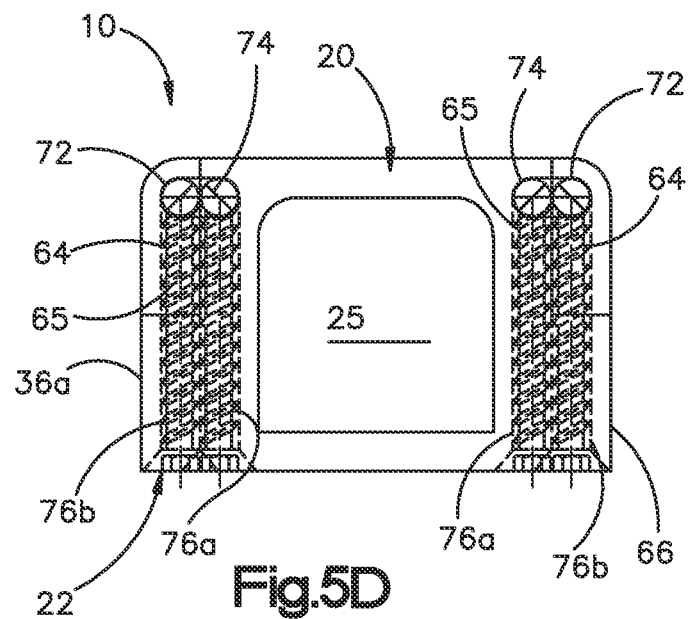
FIG. 5D is a top plan view of the intervertebral implant illustrated in FIG. 5A, but showing the fixation assembly in an extended position.
Figure 5E:
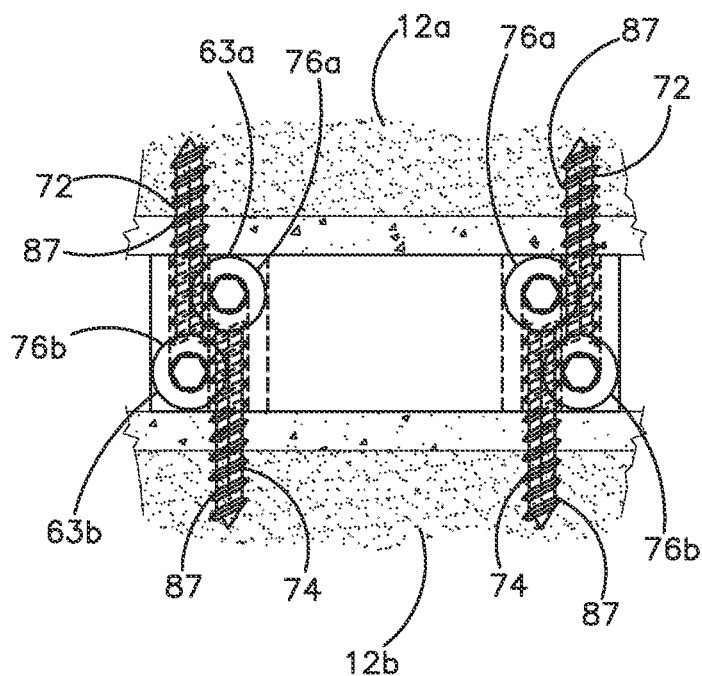
FIG. 5E is a front elevation view of the intervertebral implant as illustrated in FIG. 5D, having portions removed for the purposes of clarity, shown in an intervertebral space.
Figure 5F:
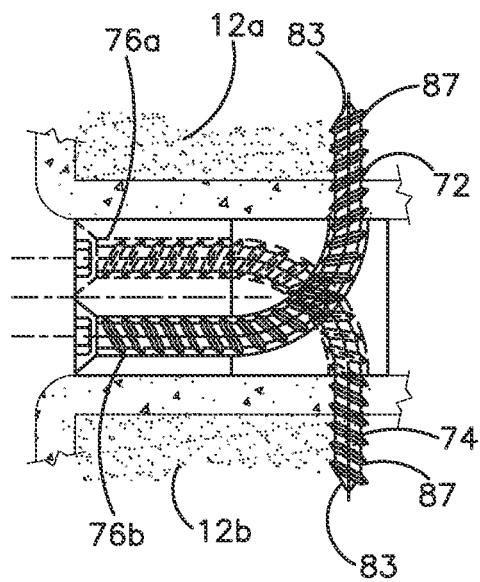
FIG. 5F is a side elevation view of the intervertebral implant as illustrated in FIG. 5D, having portions removed for the purposes of clarity.
Figure 5G:
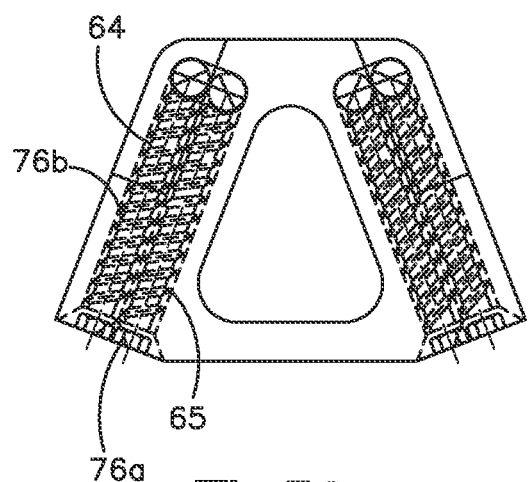
FIG. 5G is a top plan view of an intervertebral implant similar to the intervertebral implant as illustrated in FIG. 5D, but constructed in accordance with an alternative embodiment.

The channels 64 and 65 can extend substantially parallel to each other (longitudinally as illustrated in FIGS. 4A-F), or can be angularly offset with respect to each other. For instance, the channels 64 and 65 can converge toward each other along a direction from their proximal ends to their distal ends as illustrated in FIG. 4G. Alternatively still, the channels 64 and 65 can diverge away from each other along a direction from their proximal ends to their distal ends.

Referring now to FIGS. 5A-G, the fixation assembly 22 of the implant 10 is illustrated substantially as described with respect to FIGS. 4A-G, however the pins 72 and 74 can include external threads 87 along part or all of their length, for instance at the terminal end that extends transversely out from the fixation housing 36. Accordingly, as the pins 72 and 74 rotate to their extended position, the threads 87 engage the vertebral bodies 12*a* and 12*b*. The threads 87 can have a pitch that is the same or different than the pitch of the external threads 78 of the corresponding screws 76. Furthermore, the pins 72 and 74 are illustrated as integral with the screws 76*a* and 76*b*.

Referring now to FIGS. 6A-6D, the actuation assembly 22 includes a pair of fixation members 38 in the form of a first superior staple 68 and a second inferior staple 69. The first staple 68 includes a base in the form of a crossbar 70 and at least a first pair of laterally spaced pins 72 that extend out from the crossbar 70 at any location, such as at opposed outer ends of the crossbar 70 as illustrated. The second staple 69 can further include a second pair of laterally spaced pins 74 that extend out from base illustrated as a second crossbar 71 at any location, such as at opposed outer ends of the crossbar 71 as illustrated. The staples 68 and 69 can be disposed in respective superior and inferior channels 64 and 65 that can extend in any direction desired, such as the transverse direction as illustrated. It should be appreciated that the channels 64 and 65 can be continuous in a single channel, or bifurcated and separate as desired.

The actuator 40 can be provided as a screw 76 that is configured to iterate the fixation members 38 from the retracted position in which the tips 73 are recessed with respect to the fixation housing 36 and/or the implant body 20 to the extended position in which the tip 73 extend transversely out from the fixation housing 36 and/or the implant body 20. In accordance with the illustrated embodiment, the actuator 40 can be provided as a screw 76 that defines external threads 78 along part or all of its length that engages corresponding internal threads 80 of the aperture 63. Accordingly, the screw 76 can translate distally in the aperture 63 and thus the fixation housing 36 as the screw 76 is rotated in the aperture 63 relative to the fixation housing 36.

The screw 76 defines a beveled distal tip 88 that tapers transversely inwardly along a longitudinal distal direction. During operation, the screw 76 can translate from a disengaged position to an engaged position. When the screw 76 is in the disengaged position, the fixation member 38 is in the retracted position. When the screw 76 moves to the engaged position, the screw 76 moves the fixation member 38 to the extended position.

When the staples 68 and 69 are in their retracted positions, the respective crossbars 70 and 71 are disposed adjacent each other, and thus separated by a first distance that can be equal to substantially zero such that the staples 68 and 69 abut each other. The crossbars 70 and 71 can be round in cross-section or otherwise shaped so as to define respective first and second cam surfaces 90 and 92 that can extend transversely inward along a longitudinal distal direction so as to create a gap between a proximal portion of the crossbars 70 and 71 if they abut each other when in their retracted positions.

Figure 6D:
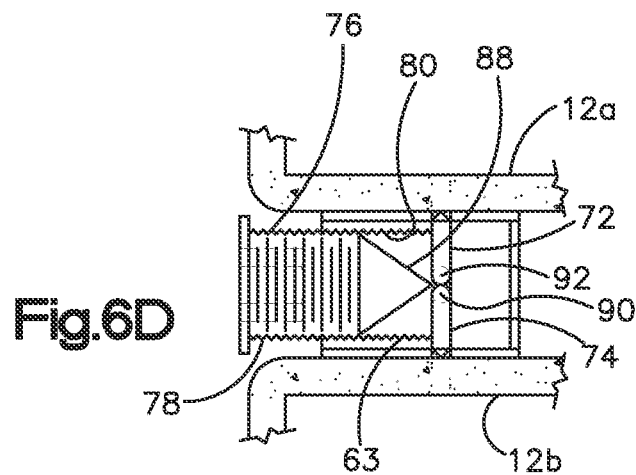
FIG. 6D is a side elevation view of the intervertebral implant as illustrated in FIG. 6C, having portions removed for the purposes of clarity.
Figure 6E:
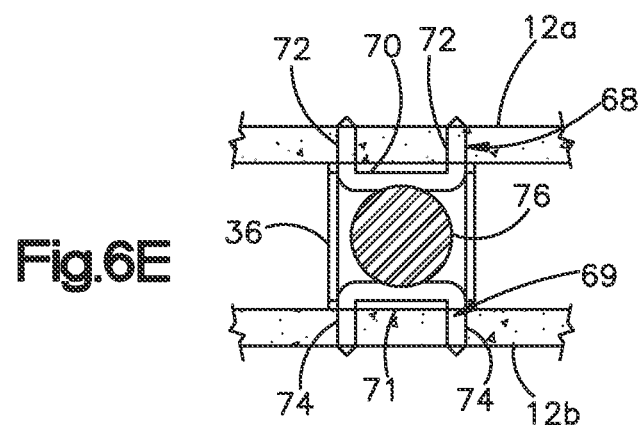
FIG. 6E is a front elevation view of the intervertebral implant as illustrated in FIG. 6A, having portions removed for the purposes of clarity, showing the fixation assembly in an extended position.
Figure 6F:
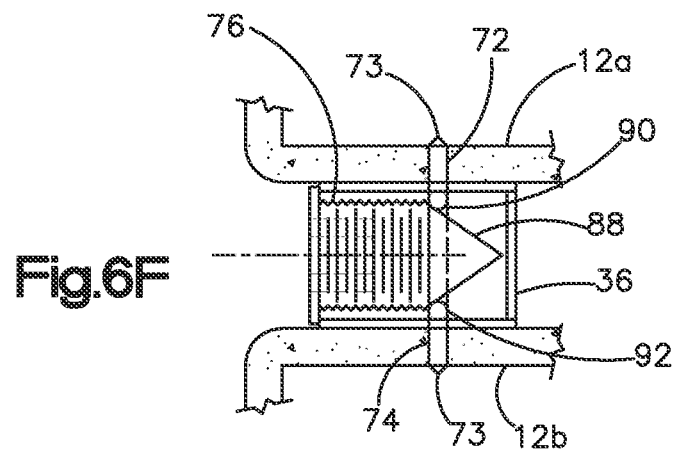
FIG. 6F is a side elevation view of the intervertebral implant as illustrated in FIG. 6E, having portions removed for the purposes of clarity.

Referring also to FIGS. 6E-F, during operation, the screw 76 translate along the longitudinally distal direction, such that the screw 76 can engage, or ride along, the first and second cam surfaces 90 and 92 of the staples 68 and 69, thereby causing the pins 72 and 74 to translate along the channel in a direction having a transverse directional component. For instance, the channels 64 and 65 can guide the pins to translate pins 72 and 74 substantially in the transverse direction with respect to the fixation housing 36. In particular, as the screw 76 translates distally in the housing, the beveled tip 88 engages the cam surfaces 90 and 92 of the staples 68 and 69. Because the beveled tip 88 is tapered, the tip 88 biases the staples 68 and 69 transversely outward as the screw 76 continues to translate distally. Thus, the beveled tip 88 can be said to define a third cam surface configured to engage the first and second cam surfaces 90 and 92 substantially simultaneously so as to cause terminal ends 73 of the pins 72 and 74 to translate in the transverse direction until the screw 76 reaches the engaged position. When the screw 76 is in the engaged position, staples 68 and 69 can be in their extended positions such that the pins 72 extend superiorly out the fixation housing 36 and the pins 74 extend inferiorly out the fixation housing 36. Accordingly, the pins 72 extend into the superior vertebral body 12a and the pins 74 extend into the inferior vertebral body 12b when the implant 10 is disposed in the intervertebral space 14. The staples 68 and 69, including the crossbars 70 and 71 and the pins 72 and 74 can be substantially rigid or flexible as desired.

It should be appreciated that the tip 88 of the screw 76 can be configured to bias the staples 68 and 69 transversely outward as the screw 76 moves in the longitudinally distal direction if either the cam surfaces 90 and 92 are angularly offset with respect to the transverse direction, or if tip 88 of the screw is angularly offset with respect to the transverse direction. In accordance with the illustrated embodiment, all cam surfaces 90 and 92 along with the cam surface defined by the beveled tip 88 are angularly offset with respect to the transverse direction. The cam surfaces can be substantially planar, curved, bent, or otherwise shaped as desired.

Figure 6G:
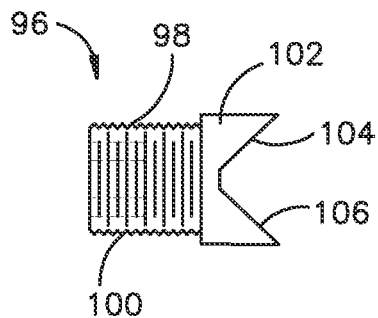
FIG. 6G is a side elevation view of an extractor of the intervertebral implant illustrated in FIG. 6A, configured to iterate the fixation assembly to the retracted position.
Figure 6H:
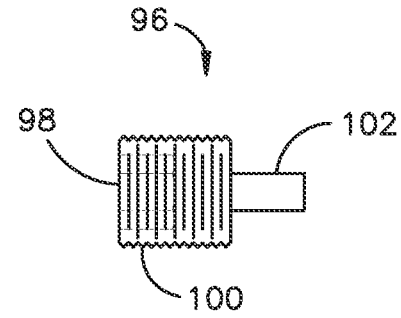
FIG. 6H is a top plan view of the extractor illustrated in FIG. 6G.
Figure 6I:
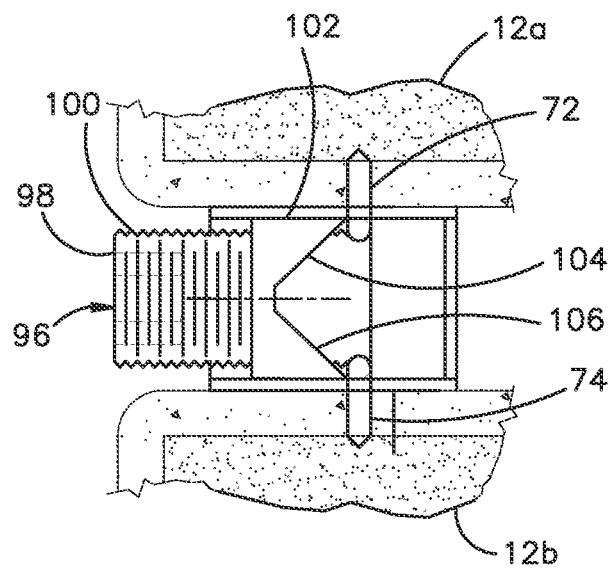
FIG. 6I is a side elevation view of the implant as illustrated in FIG. 6A, showing the extractor installed with the fixation assembly in an extended position, having portions removed for the purposes of clarity.
Figure 6J:
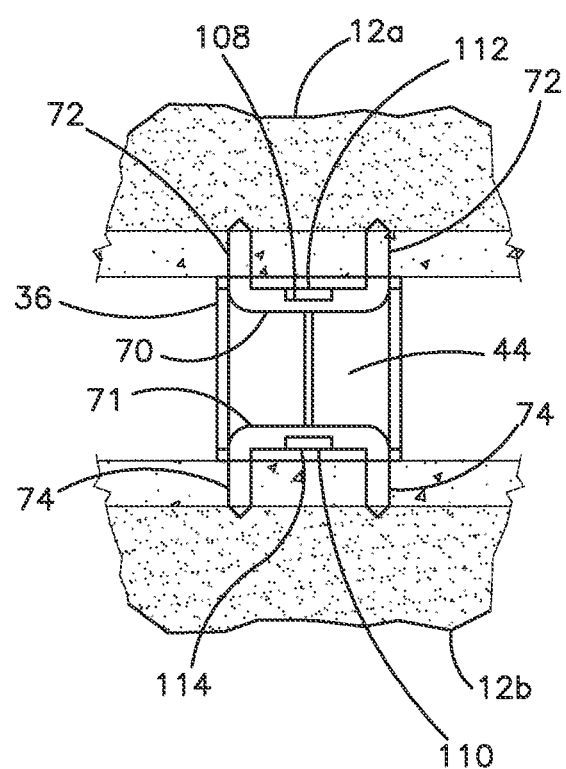
FIG. 6J is a front elevation view of the intervertebral implant as illustrated in FIG. 6I, having portions removed for the purposes of clarity.
Figure 6K:
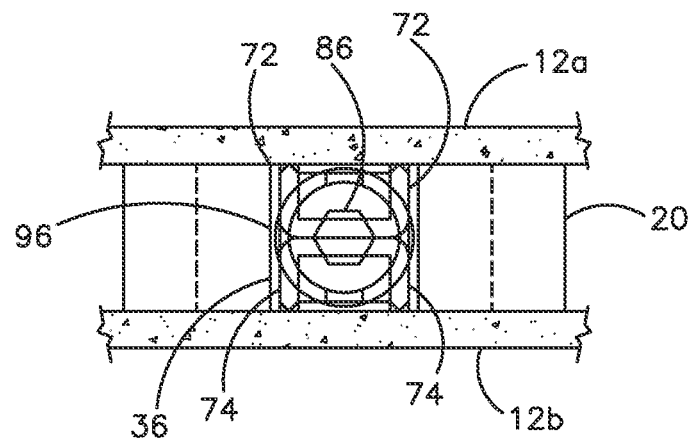
FIG. 6K is a front elevation view of the intervertebral implant as illustrated in FIG. 6I, showing an actuator of the fixation assembly, and showing the fixation assembly in a retracted position.
Figure 6L:
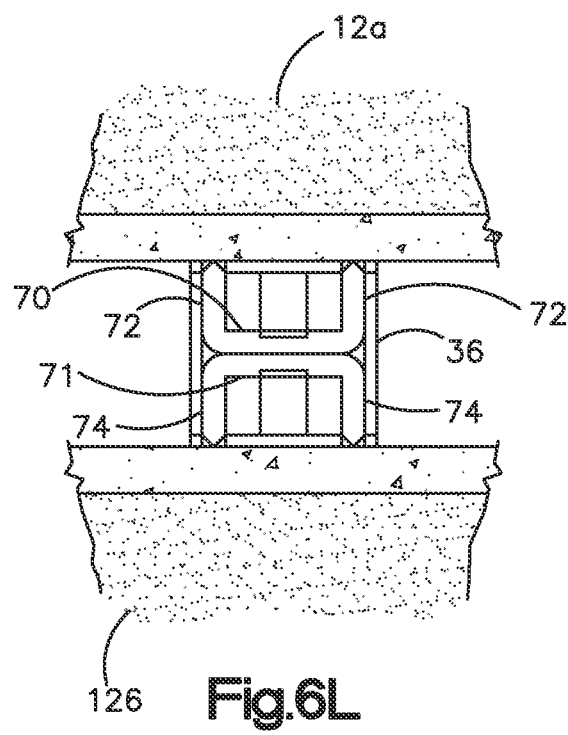
FIG. 6L is a front elevation view of the intervertebral implant as illustrated in FIG. 6K, but showing portions removed for the purposes of clarity.
Figure 6M:
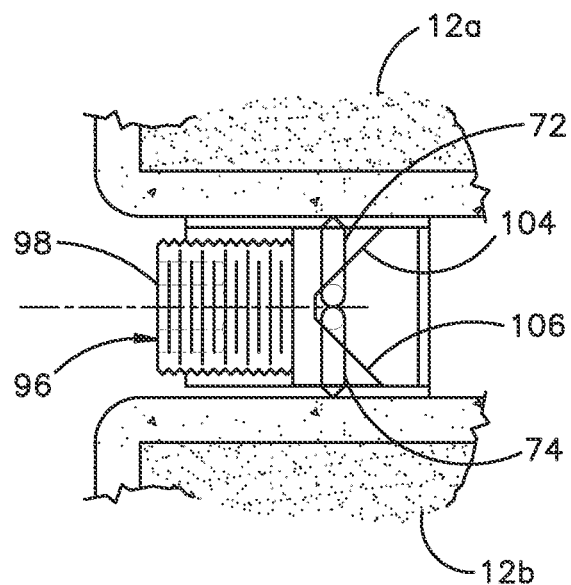
FIG. 6M is a side elevation view of the intervertebral implant as illustrated in FIG. 6L, showing portions removed for the purposes of clarity.
Figure 6N:
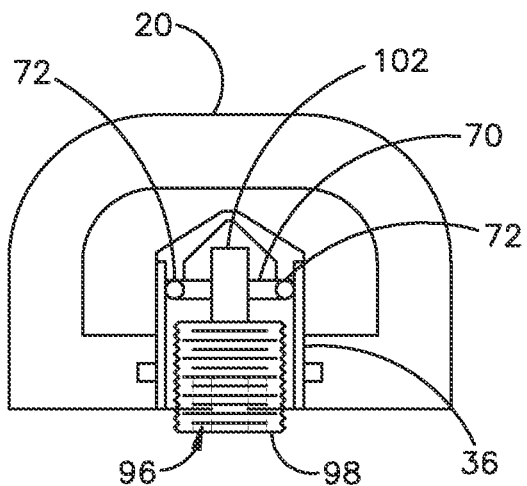
FIG. 6N is a top plan view of the intervertebral implant as illustrated in FIG. 6M, showing portions removed for the purposes of clarity.

Referring now also to FIGS. 6G-H, the fixation assembly 22 can further include a second actuator in the form of an extractor 96 that is configured to engage the crossbars of the first and second staples 68 and 69 so as to cause terminal ends 73 of the pins 72 of the first staple 68 to retract inferiorly into the fixation housing 36 and further to cause the terminal ends 73 of the pins 74 of the second staple 69 to retract superiorly into the housing.

The extractor 96 can be provided as a screw 98 that defines an externally threaded shaft 100 along part or all of its length that engages the internal threads 80 of the aperture 63 in the fixation housing 36. Accordingly, the screw 98 can translate distally in the aperture 63 and thus the fixation housing 36 as the screw 98 is rotated in the aperture 63 relative to the fixation housing 36. The screw 98 further defines a collar 102 at its distal end that is rotatable with respect to the threaded shaft 10. The collar 102 defines at least one beveled surface such as a pair of beveled surfaces 104 and 106 that can be angularly offset with respect to the transverse direction. In accordance with the illustrated embodiment, the beveled surfaces 104 and 106 are tapered toward each other along a proximal direction opposite the distal direction of insertion of the screw 98.

The crossbars 70 and 71 can define respective first and second extraction cam surfaces 108 and 110 that are configured to engage the beveled surfaces 104 and 106, respectively, of the extractor 96. The extraction cam surfaces 108 and 110 can be provided by notches 112 and 114 that extend transversely inward into, but not through, the transverse outer surfaces of the crossbars 70 and 71. The notches 112 and 114 can be sized so as to receive the respective beveled surfaces 104 and 106. The extraction cam surfaces 108 and 110 can be angularly offset with respect to the transverse direction, or can extend in any direction as desired. The extraction cam surfaces 108 and 110, and the beveled surfaces 104 and 106 can extend substantially planar, can be curved, bent, or otherwise shaped as desired.

During operation, the screw 76 can be removed after the staples 68 and 69 have been iterated to their extended positions, or otherwise out from their retracted positions. The screw 98 can translate distally in the fixation housing 36 from a disengaged position to an engaged position. When the screw 98 is in the disengaged position, the staples 68 and 69 remain in their extended position as actuated by the screw 76. When the screw 98 moves to the engaged position, the screw 98 iterates the staples 68 and 69 to their retracted positions. In particular, as the screw 98 translates from the disengaged position to the engaged position, the beveled surfaces 104 and 106 contact the crossbars 70 and 71, for instance in the notches 112 and 114, which can remain in the fixation housing 36 when the staples 68 and 69 are in their fully extended positions.

Because the collar 102 is rotatable with respect to the threaded screw shaft 100, the beveled surfaces 104 and 106 remain engaged in the notches 112 and 114 as the screw shaft 100 continues to rotate with respect to the fixation housing 36 to translate the screw 98 distally in the fixation housing 36. The fixation housing 36 can define a channel that receives the collar so as to maintain the beveled surfaces 104 and 106 in alignment with the notches 112 and 114 as the screw 98 rotates in the fixation housing 36. As the screw 98 translates distally, the crossbars 70 and 71 ride along the beveled surfaces 104 and 106. The beveled surfaces 104 therefore bias the staples 68 and 69 so as to move transversely inward toward the central longitudinal axis 37. Thus, the superior staple 68 and corresponding pins 72 translate inferiorly until the pins 72 are removed from the superior vertebral body 12a and recessed in the fixation housing 36. The implant 10 can then be removed from the intervertebral space 12 or repositioned in the intervertebral space 12 as desired. Furthermore, the inferior staple 69 and corresponding pins 74 translate superiorly until the pins 74 are removed from the inferior vertebral body 12b and recessed in the fixation housing. Thus, the beveled surfaces 104 and 106 can be referred to as cam surfaces that cause the fixation members 38 to move in a direction from their extended positions toward their retracted positions.

In accordance with the illustrated embodiment, the extractor 96 can be provided as a discrete actuator with respect to the actuator 40. In accordance with an alternative embodiment, the extractor 96 can be attachable to the actuator 40 or integrally formed with the actuator 40, such that one longitudinal side of the actuator 40 defines the distal tip 88 and the opposed longitudinal side of the actuator 40 includes the collar 102.

Figure 7A:
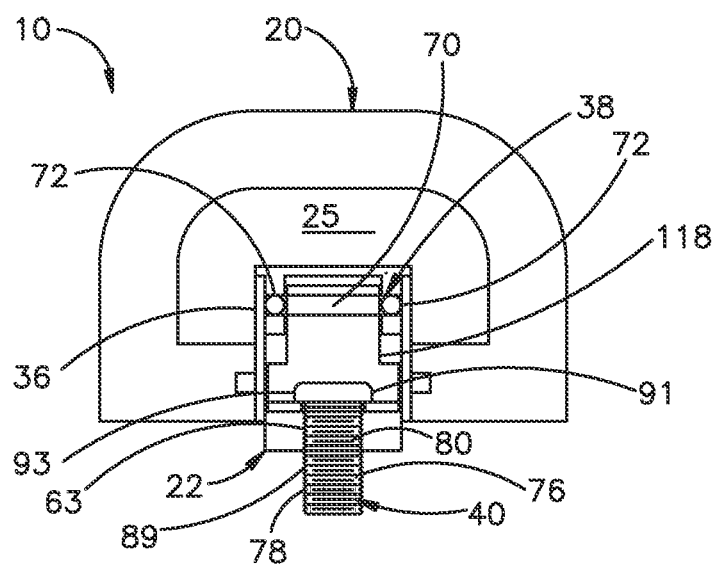
FIG. 7A is a top plan view of an intervertebral implant including an implant body and a fixation assembly constructed in accordance with an alternative embodiment, having portions removed for the purposes of clarity, showing the fixation assembly in a retracted position.
Figure 7B:
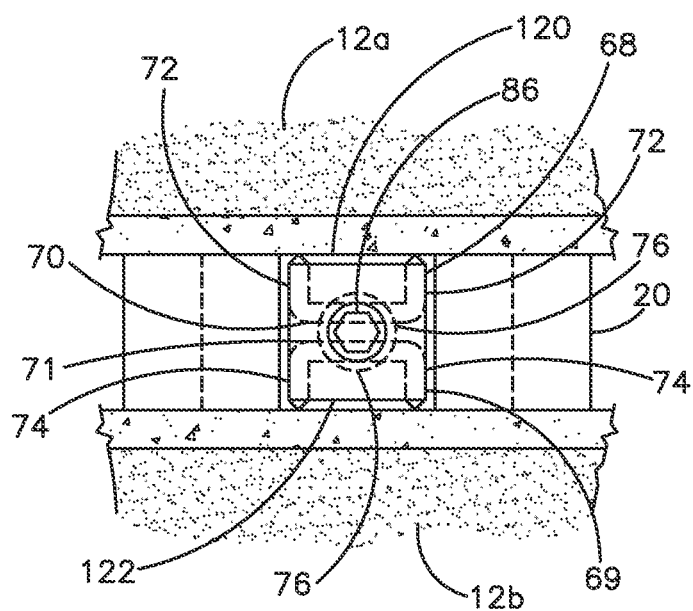
FIG. 7B is a front elevation view of the intervertebral implant as illustrated in FIG. 7A, showing portions removed for the purposes of clarity, disposed in an intervertebral space.
Figure 7C:
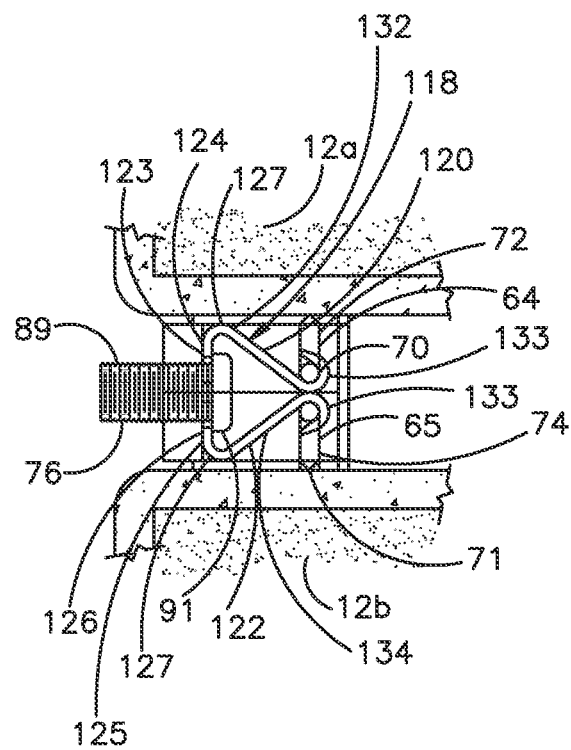
FIG. 7C is a side elevation view of the intervertebral implant as illustrated in FIG. 7B, showing portions removed for the purposes of clarity.

Referring now to FIGS. 7A-C, the fixation assembly 22 can be constructed in accordance with an alternative embodiment. The fixation assembly 22 can include at least one actuator 40 that is configured to iterate at least one fixation member 38 between a retracted position and an extended position in the manner described above. The fixation assembly 22 can further include a biasing member 118 that is operably coupled between the actuator 40 and the fixation member 38. For instance, the biasing member 118 can be attached to the fixation member 38 at its distal end, and can move the fixation member 38 from the retracted position to the extended position under forces applied to the biasing member 118 by the actuator 40.

The at least one fixation member 38 can be in the form of a first superior fixation member illustrated as a first superior staple 68, and a second inferior fixation member illustrated as a second inferior staple 69 as described above. Thus, the first staple 68 includes a base in the form of a crossbar 70 and at least a first pair of laterally spaced pins 72 that extend out from the crossbar 70 at any location, such as at opposed outer ends of the crossbar 70 as illustrated. The second staple 69 can further include a second pair of laterally spaced pins 74 that extend out from a base in the form of a second crossbar 71 at any location, such as at opposed outer ends of the crossbar 71 as illustrated. The staples 68 and 69 can be disposed in respective superior and inferior channels 64 and 65 that can extend in any direction desired, such as the transverse direction as illustrated. It should be appreciated that the channels 64 and 65 can be continuous in a single channel, or bifurcated and separate as desired.

In accordance with the illustrated embodiment, the actuator 40 can be provided as a screw 76 that defines external threads 78 along part or all of the longitudinal length of the screw shaft 89. The screw 76 defines a screw head 91 that defines an outer cam surface 93 and is coupled to the distal end of the screw shaft 89, and can have a cross-sectional dimension (e.g., diameter) greater than that of the screw shaft 89. The threads 78 engage corresponding internal threads 80 of the aperture 63 in the front end 42 of the fixation housing 36. Accordingly, the screw 76 can translate distally in the aperture 63 and thus the fixation housing 36 as the screw 76 is rotated in the aperture 63 relative to the fixation housing 36. During operation, the screw 76 can translate from a disengaged position to an engaged position. When the screw 76 is in the disengaged position, the fixation member 38 is in the retracted position. When the screw 76 moves to the engaged position, the screw 76 moves the fixation member 38 to the extended position.

The biasing member 118 includes a first superior flexible biasing arm 120 and a second inferior flexible biasing arm 122. The arms 120 and 122 define respective proximal ends 124 and 126 that extend transversely inward with respect to a pair of intermediate segments 132 and 134 that are tapered transversely toward each other along the distal longitudinal direction. The proximal ends 124 and 126 are fixed to the fixation housing 36 at respective connection locations 123 and 125 via an adhesive, mechanical fastener, or friction fit, or any suitable alternative fixation. The arms 120 and 122 define distal ends in the form of hooks 133 that are fastened to the crossbars 70 and 71. The intermediate segments 132 and 134 are connected between the proximal and distal ends of the flexible arms 120 and 122. The intermediate segments 132 and 134 are connected to the proximal ends 124 and 126 by a hinge 127. The hooks 133 are transversely spaced from each other by a distance, which can equal zero if they abut, that is less than the transverse dimension of the screw cam surface 93 when the staples 68 and 69 are in their retracted positions.

Figure 7D:
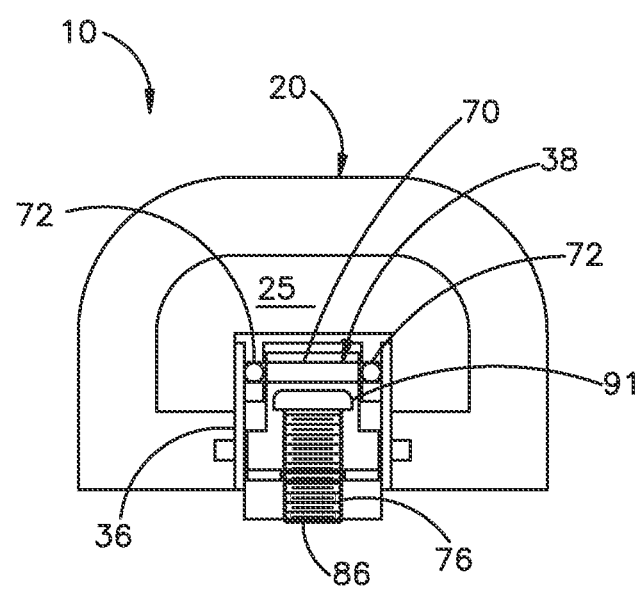
FIG. 7D is a top plan view of the intervertebral implant illustrated in FIG. 7A, showing the fixation assembly in an extended position.
Figure 7E:
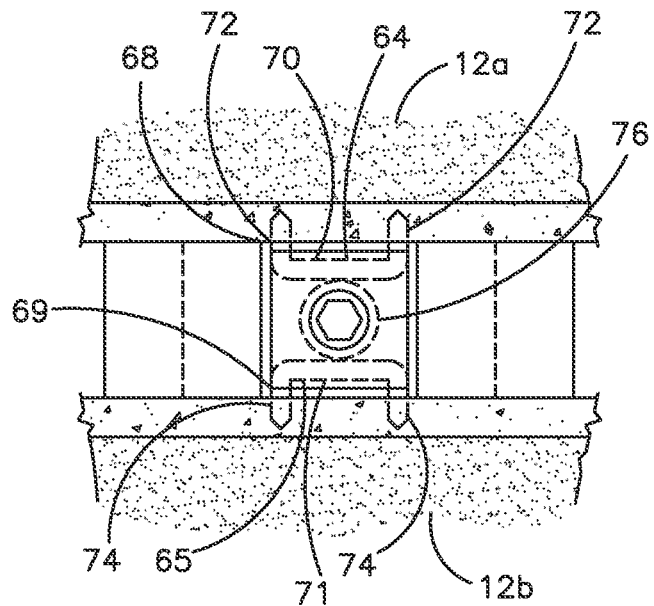
FIG. 7E is a front elevation view of the intervertebral implant as illustrated in FIG. 7D, showing portions removed for the purposes of clarity, disposed in an intervertebral space.
Figure 7F:
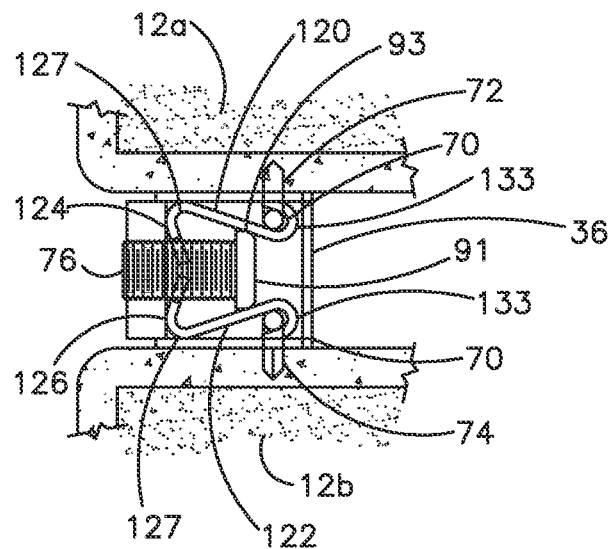
FIG. 7F is a side elevation view of the intervertebral implant as illustrated in FIG. 7E, showing portions removed for the purposes of clarity.

Referring also to FIGS. 7D-F, as the screw 76 translates distally from its disengaged position to its engaged position, the outer cam surface 93 of the screw 76 is configured to contact and ride along the flexible arms 120 and 122 substantially simultaneously. The flexible arms 120 and 122 can thus define inner cam surfaces that engage the outer cam surface 93 of the screw 76. The outer cam surface 93 defines a transverse dimension such that as the cam surface 93 rides along the intermediate segments 132 and 134, the flexible arms 120 and 122 flex transversely outward about the hinge 127, thereby causing the hooks and corresponding pins 72 and 74 to translate transversely outward in their respective channels 64 and 65 to their extended positions as illustrated in FIG. 7F, whereby the terminal tips 73 of the pins 72 extends superiorly out the fixation housing 36, and the terminal tips 73 of the pins 74 extend inferiorly out the fixation housing 36. In this regard, the inner transverse surfaces of the intermediate segments 132 and 134 can be referred to as cam surfaces.

Figure 8B:
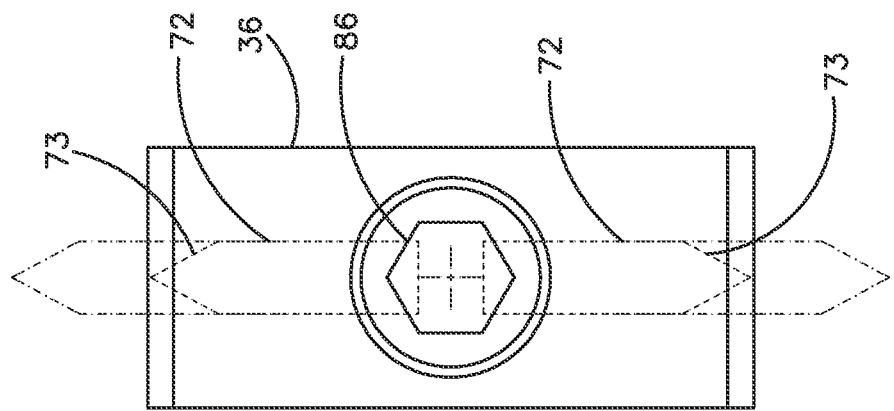
FIG. 8B is a front elevation view of the intervertebral implant illustrated in FIG. 8A.
Figure 8A:
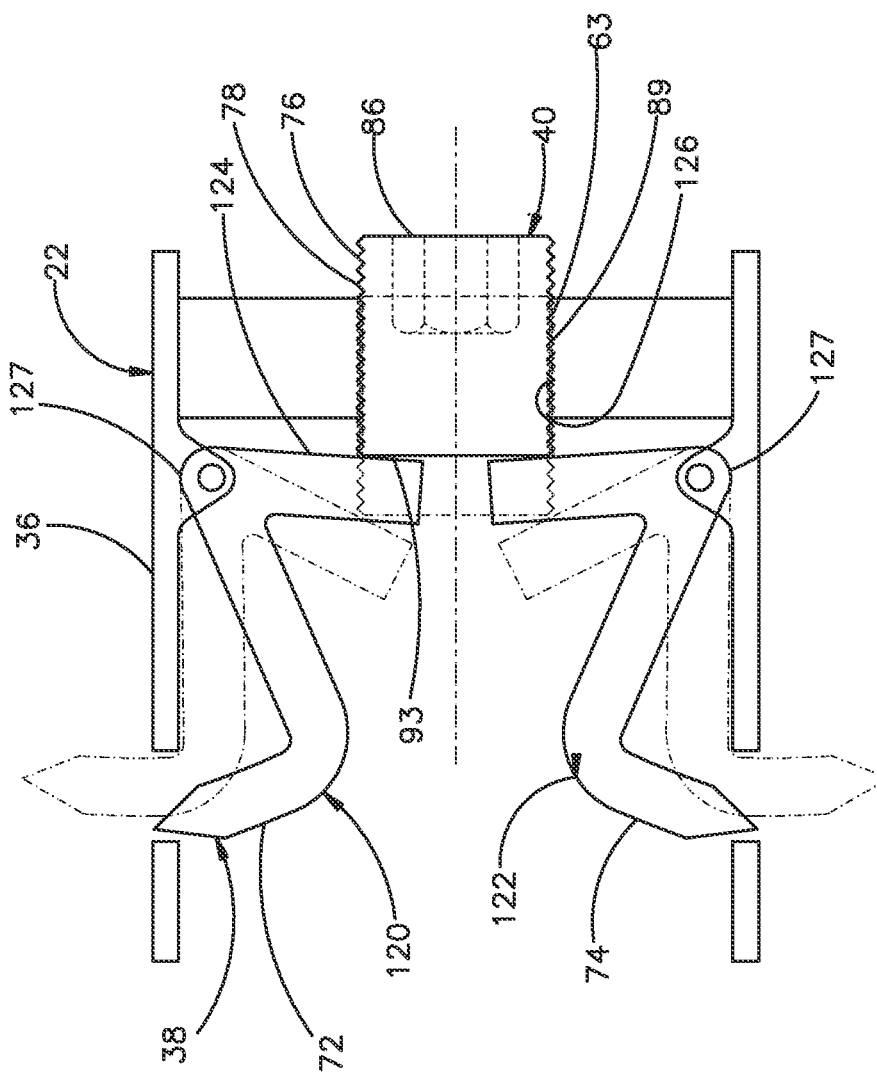
FIG. 8A is a side elevation view of an intervertebral implant similar to the intervertebral implant illustrated in FIG. 7A, but constructed in accordance with an alternative embodiment, having portions removed for the purposes of clarity.

Referring now to FIG. 8A-B, the biasing arms 120 and 122 can alternatively be substantially rigid so as to not flex in response to engagement by the actuator 40. In particular, the biasing arms 120 and 122 are pivotally connected to the fixation housing 36, for instance at the hinges 127. Thus, the biasing arms 120 and 122 can pivot relative to the fixation housing 36 about a lateral pivot axis. The proximal ends 124 and 126 can be detached from the flex housing 36, and are disposed in the aperture 63 in accordance with the illustrated embodiment. The distal ends can be provided as hooks that are connected to fixation members as described above with respect to FIGS. 7A-F, or can alternatively include integral fixation pins 72 and 74, respectively.

The actuator 40 can be provided as a screw 76 that defines external threads 78 along part or all of the length of a screw shaft 89 that engages corresponding internal threads 80 of the aperture 63. Accordingly, the screw 76 can translate distally in the aperture 63 and thus the fixation housing 36 as the screw 76 is rotated in the aperture 63 relative to the fixation housing 36. During operation, the screw 76 can translate distally from a disengaged position to an engaged position. The distal end of the screw 76 can define a cam surface 93 that is sized to contact the proximal ends 124 and 126 of the biasing arms 120 and 122. Thus, the longitudinal proximal surfaces of the proximal ends 124 and 126 present respective cam surfaces that are configured to receive a longitudinal biasing force that causes the biasing arms 120 and 122 to pivot, which in turn causes the superior and inferior fixation pins 72 and 74, respectively, to extend superior and inferior of the housing 36 into the respective superior and inferior vertebral bodies 12a and 12b.

Figure 9A:
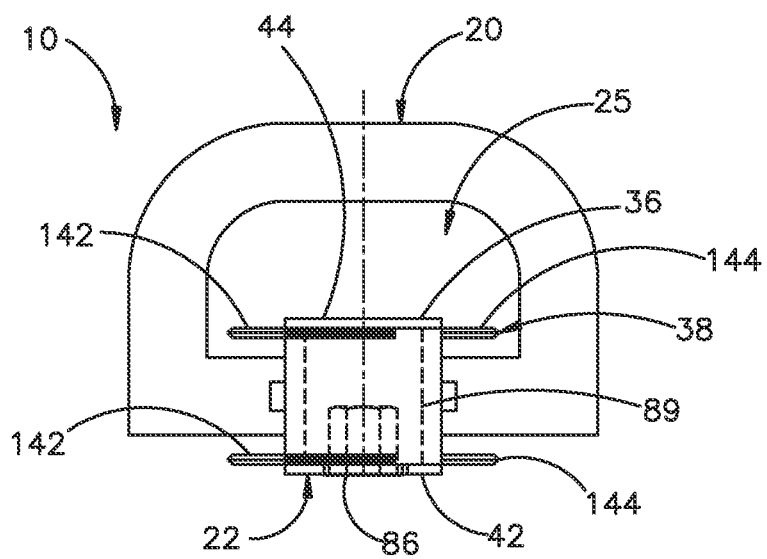
FIG. 9A is a top plan view of an intervertebral implant including an implant body and a fixation assembly constructed in accordance with an alternative embodiment, having portions removed for the purposes of clarity, showing the fixation assembly in a retracted position.
Figure 9B:
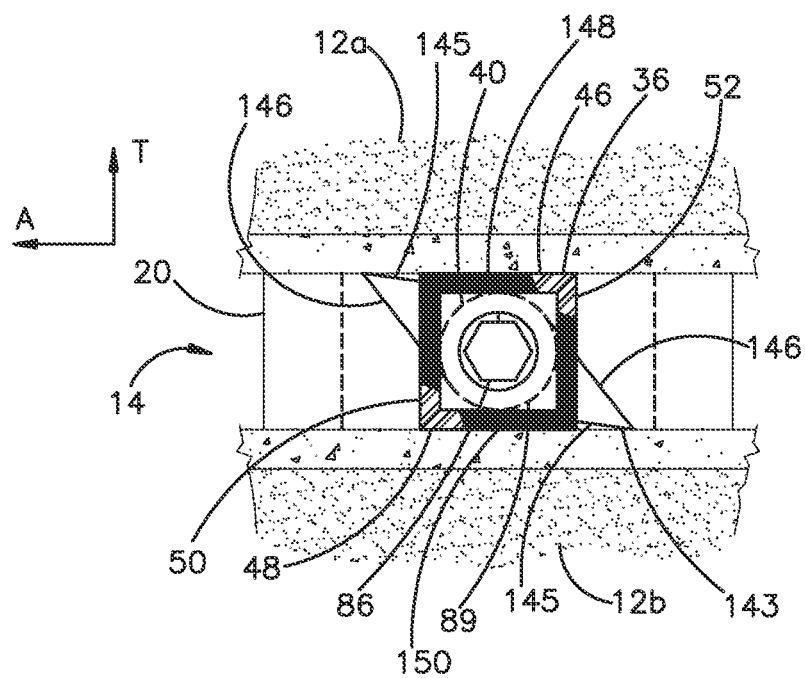
FIG. 9B is a front elevation view of the intervertebral implant as illustrated in FIG. 9A, having portions removed for the purposes of clarity, shown in an intervertebral space.

Referring now to FIGS. 9A-B, the fixation assembly 22 can be constructed generally as a propeller in accordance with an alternative embodiment. The fixation housing 36 can be positioned such that the rear end 44 is aligned with the central opening 25 of the implant body 20 and the front end 42 is displaced proximal of the front end 24 of the implant body 20. The fixation assembly 22 includes an actuator 40 in the form of a rotatable hub or shaft 89 that is connected to the fixation housing 36 so as to be rotatable with respect to the fixation housing 36 and translatably fixed to the housing. The rotatable shaft 89 can be threaded or unthreaded, and can be configured so as to maintain a substantially fixed longitudinal position (and thus does not substantially translate proximally or distally) as it rotates relative to the fixation housing 36. The shaft 89 defines an engagement member illustrated as a socket 86 that extends longitudinally into the proximal end of the shaft 89. The socket 86 is illustrated as a hexagonal in shape, though it could be shaped as any suitable polygonal shape, including a "plus" shape, a "dash" shape, or any alternative shape as desired so as to receive a drive member that actuates the shaft to rotate.

The at least one fixation member 38 can include at least one pair of fixation blades such as first superior fixation blade 142 and a second inferior fixation blade 144 that are rotatably coupled to the shaft 89 such that the blades 142 and 144 rotate along with the shaft 89. In accordance with the illustrated embodiment, the fixation member 38 includes a first proximal pair of a superior blade 142 and an inferior blade 144, and a second distal pair of a superior blade 142 and an inferior blade 144. The first pair of blades 142 and 144 is disposed proximal of the front end 24 of the implant body 20, and the second pair of blades 142 and 144 is disposed in alignment with the central cavity 25 of the implant body 20. Both pairs of blades 142 and 144 can be rotatably coupled to the shaft 89 so as to rotate along with the shaft 89. The blades 142 and 144 can be substantially planar in the lateral and transverse directions A and T, or can be curved if desired (for instance if the blades 142 and 144 are translatable with respect to the shaft 89, or of the shaft 89 is translatable with respect to the fixation housing 36. The blades 142 and 144 can taper to a distal terminal tip 143. Each blade 142 and 144 presents a leading edge 145 and a trailing edge 146 with respect to movement from the retracted position to the extended position.

Figure 9C:
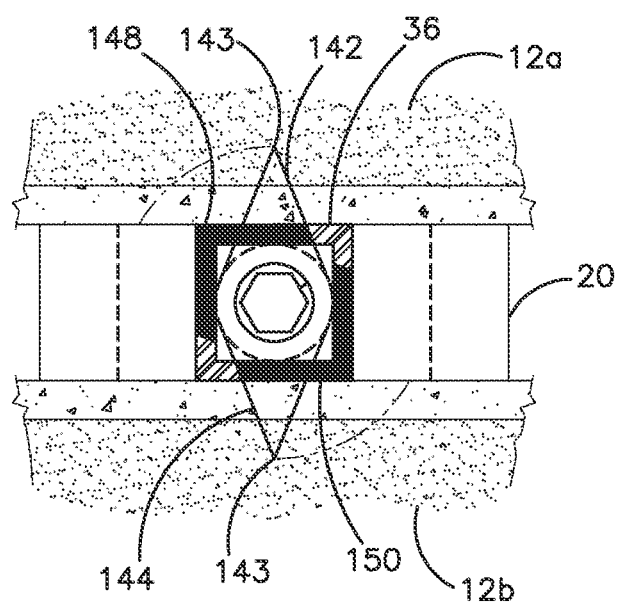
FIG. 9C is a front elevation view of the intervertebral implant illustrated in FIG. 9B, having portions removed for the purposes of clarity, showing the fixation assembly in an extended position.

Referring also to FIG. 9C, the fixation housing 36 defines a channel illustrated as a slot that allows the blades 142 and 144 to rotate from their retracted positions to their extended positions. In particular, the fixation housing 36 defines a superior blade slot 148 that receives the superior blade 142 and an inferior blade slot 150 that receives the inferior blade 144. The inferior and superior blade slots 148 and 150 are both laterally and transversely opposed, and dimensioned such that the blades 142 and 144 can rotate from a first retracted position whereby the tips 143 are transversely recessed with respect to the vertebral bodies 12a and 12b, respectively, for instance in the fixation housing 36 to a second extended position whereby the tips 143 extend transversely out from the fixation housing 36 and into the respective vertebral bodies 12a and 12b when the implant 10 is disposed in the intervertebral space 14. For instance, the slots 148 extend through both the top and lateral ends 46 and 50 of the fixation housing body 36. The slots 150 extend through both the bottom and lateral ends 48 and 52 of the fixation housing 36. The first pair of slots 148 and 150 is disposed proximal of the front end of the fixation housing 36, and the second pair of slots 148 and 150 is aligned with the central cavity 25.

During operation, the shaft 89 rotates from a first rotational disengaged position whereby the fixation blades 142 and 144 are in the recessed position to an second rotational engaged position whereby the fixation blades 142 and 144 are in the extended position. The shaft 89 can rotate along an angle between 0 degrees and 180 degrees, such as between 20 degrees and 90 degrees, between the disengaged and the engaged position. The blades 142 and 144 can extend radially out from the shaft 89 through the respective blade slots 148 and 150 such that the tips 143 are disposed laterally out from the fixation housing in the intervertebral space 14 when the blades 142 and 144 are in their retracted positions. The fixation housing 36 provides stops at the lateral ends of the slots 148 and 150 in the top and bottom ends 46 and 50 that prevent the blades 142 and 144 from over-rotating past the extended positions.

Figure 9D:
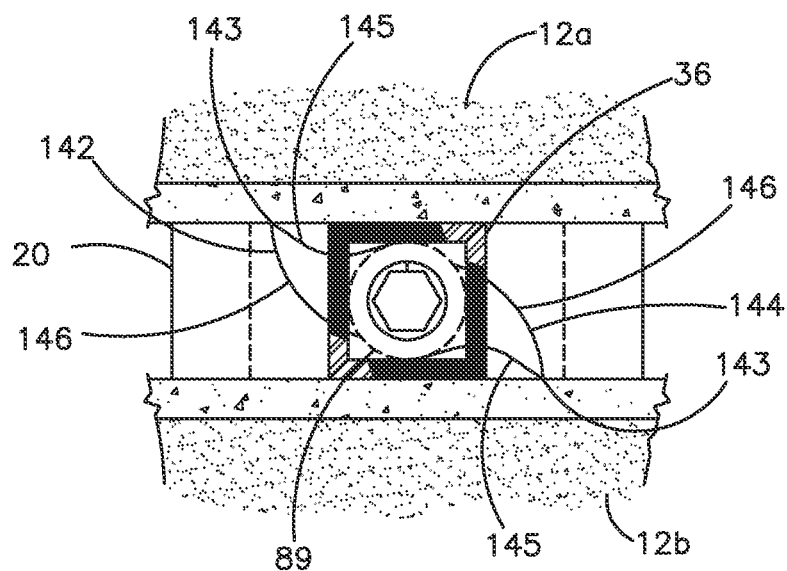
FIG. 9D is a front elevation view of an intervertebral implant similar to that illustrated in FIG. 9B, but showing a bone fixation member of the fixation assembly constructed in accordance with an alternative embodiment.
Figure 9E:
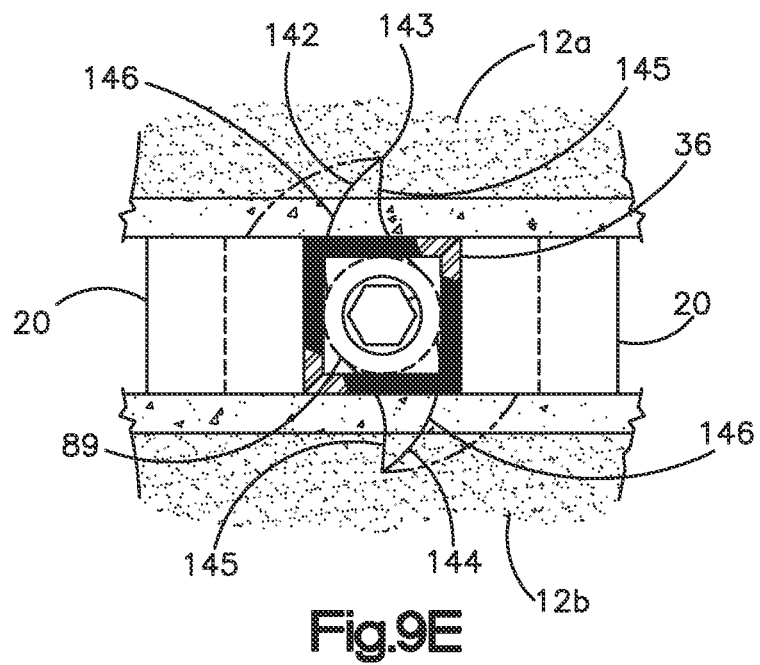
FIG. 9E is a front elevation view of the intervertebral implant as illustrated in FIG. 9D, showing the fixation assembly in an extended position.

As illustrated in FIGS. 9A-C, the leading and trailing edges 145 and 146 can extend substantially straight in a radially outward direction from the shaft 89 to the tips 143. Alternatively, one or both of the leading and trailing edges 145 and 146 can be curved as desired in a radially outward direction from the shaft 89 toward the tips 143. For instance, as illustrated in FIGS. 9D-E, the leading edges 145 can be concave and the trailing edges 146 can be convex. Alternatively, either or both of the leading and trailing edges 145 and 146 can be straight, concave, convex, or otherwise curved as desired.

Referring now to FIGS. 10A-C, the fixation assembly 22 is constructed substantially as described with respect to the fixation assembly as illustrated in FIGS. 9A-C. However, the fixation blades 142 and 144 as illustrated in FIGS. 10A-C can be constructed extend radially out from the shaft 89 a distance less than that of the blades 142 and 144 as illustrated in FIGS. 9A-C. Therefore, when the blades 142 and 144 are in their retracted positions, the blades 142 and 144 are disposed in the fixation housing 36. The superior blade slots 148 can extend through the top end 46 of the fixation housing 36 and not through either lateral end of the fixation housing. Likewise, the inferior blade slots 150 can extend through the top end 46 of the fixation housing 36 and not through either lateral end of the fixation housing.

Referring now to FIGS. 11A-B, the fixation assembly 22 can include the rotatable shaft 89 supported in the fixation housing 36 substantially as described above with respect to FIGS. 9A-C. Thus, the fixation assembly 22 includes an actuator 40 in the form of a rotatable shaft 89 that is connected to the fixation housing 36 so as to be rotatable with respect to the fixation housing 36 and translatably fixed to the housing. The rotatable shaft 89 can be threaded or unthreaded, and can be configured so as to maintain a substantially fixed longitudinal position (and thus does not substantially translate proximally or distally) as it rotates relative to the fixation housing 36. The shaft 89 defines an engagement member illustrated as a socket 86 that extends longitudinally into the proximal end of the shaft 89. The socket 86 is illustrated as a hexagonal in shape, though it could be shaped as any suitable polygonal shape, including a "plus" shape, a "dash" shape, or any alternative shape as desired so as to receive a drive member that actuates the shaft to rotate.

The shaft 89 defines an outer circumferential surface 141 and at least one groove 147 that extends radially into the circumferential surface 141 and receives at least one fixation member 38, such as a pair of fixation members 38. The shaft 89 can alternatively define a pair of longitudinally spaced grooves. The groove 147 can extend around a portion of or the entirety of the circumference of the shaft 89, or can alternatively include a pair of discrete grooves that each receives a pair of fixation members 38.

The at least one fixation member 38 can include a first superior staple 68 and a second inferior staple 69 coupled to the shaft 89 in the first proximal groove 147, and a first superior staple 68 and a second inferior staple 69 coupled to the shaft 89 in the second distal groove 147. The staples 68 and 69 can extend out from the shaft 89 in respective superior and inferior channels 64 and 65 that extend into or through the fixation housing 36. The first staple 68 includes a base in the form of a crossbar 70 and at least a first pair of laterally spaced pins 72 that extend out from the crossbar 70 at any location, such as at opposed outer ends of the crossbar 70 as illustrated. The second staple 69 can further include a second pair of laterally spaced pins 74 that extend out from base illustrated as a second crossbar 71 at any location, such as at opposed outer ends of the crossbar 71 as illustrated. The staples 68 and 69 can be disposed in respective superior and inferior channels 64 and 65 that can extend in any direction desired, such as the transverse direction as illustrated. It should be appreciated that the channels 64 and 65 can be continuous in a single channel, or bifurcated and separate as desired. The staples 68 and 69 can define terminal tips 73 that can be rigid, and extend tangentially out from the shaft 89 and into the respective channels 64 and 65. At least a portion of the proximal portion of the staples 68 and 69 can be flexible so as to wrap around the shaft 89 when the staples 68 and 69 are in the retracted position, and extend tangentially out from the shaft 89 when the staples 68 and 69 are in the extended position.

Referring also to FIG. 11C, during operation, the shaft 89 rotates from a first rotational disengaged position whereby the staples 68 and 69 are in the recessed position to an second rotational engaged position whereby the staples 68 and 69 are in the extended position. The staples 68 and 69 can travel in their respective channels 64 as they move from their retracted positions to their extended positions. When the staples 68 and 69 are in the retracted positions, the tips 63 are disposed in the housing 36 and do not extend into the respective vertebral bodies 12a and 12b. When the staples 68 and 69 are moved to the extended positions, the tips 63 extend transversely out from the fixation housing 36 and into the vertebral bodies 12a and 12b. The fixation housing 36 can provide any suitable stop that prevents the shaft 89 from over-rotating past the engaged position.

Referring now to FIGS. 11D-F, the tips 73 of the staples 68 and 69 can be flexible, and can be disposed substantially entirely in the groove 147 of the shaft 89 when the shaft 89 is in the disengaged position and the staples 68 and 69 are in the corresponding retracted position. Thus, when the shaft 89 rotates from the disengaged position to the engaged position, the tips 73 extend into the respective channels 64 and 65 until the shaft 89 is in the engaged position which causes the staples 68 and 69 to move to the extended position such that the tips 73 extend out from the fixation housing 36 and into the adjacent vertebral bodies 12a and 12b.

Referring to FIGS. 12A-C, the fixation assembly 22 can be constructed substantially as described above with respect to FIGS. 11A-C, however the shaft 89 can include gear teeth 152 that are longitudinally elongate and circumferentially spaced about the outer circumference 141 of the shaft 89. The staples 68 can include a complementary rack 154 of teeth 156 that are configured to mate with the gear teeth 152 of the shaft 89 as the shaft rotates so as to drive the tips 73 into the vertebral bodies 12a and 12b in the manner described above. The rack 154 can be flexible, and the tips 73 can be flexible or rigid as desired. It should be appreciated that the shaft 89 can be rotated in an opposite direction from the engaged position to the disengaged position so as to cause the staples 68 and 69 to retract from the extended position to the retracted position.

Figure 13A:
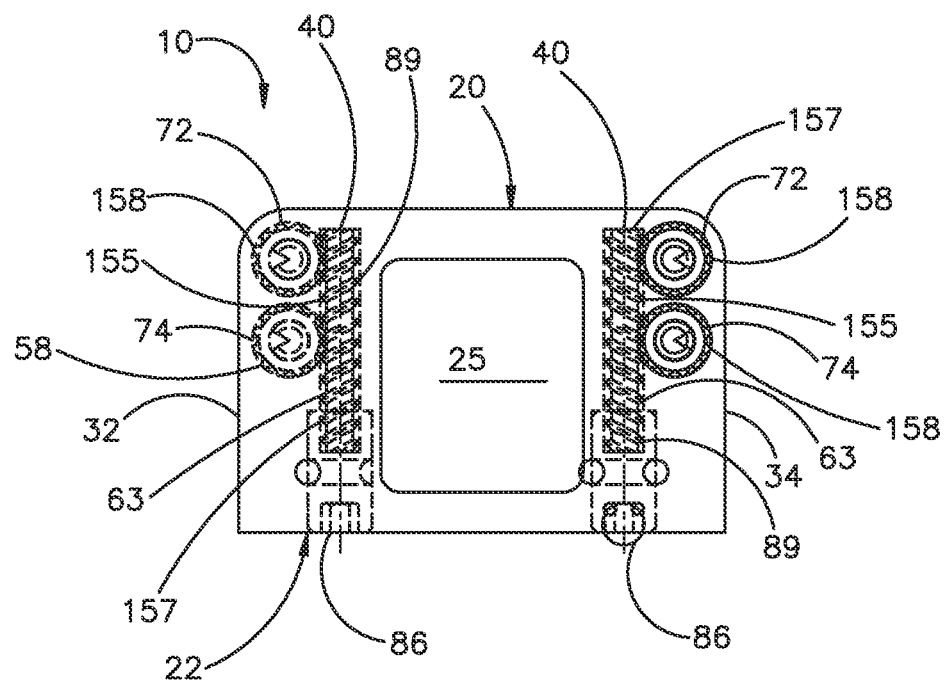
FIG. 13A is a top plan view of an intervertebral implant including an implant body and a fixation assembly constructed in accordance with an alternative embodiment, having portions removed for the purposes of clarity, showing the fixation assembly in a retracted position.
Figure 13B:
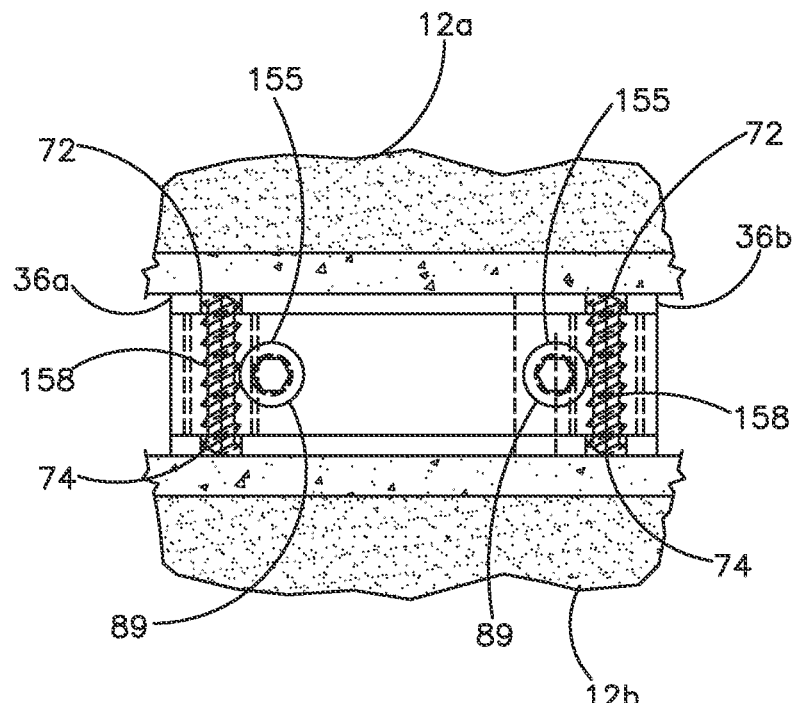
FIG. 13B is a front elevation view of the intervertebral implant as illustrated in FIG. 13A, having portions removed for the purposes of clarity, shown in an intervertebral space.
Figure 13C:
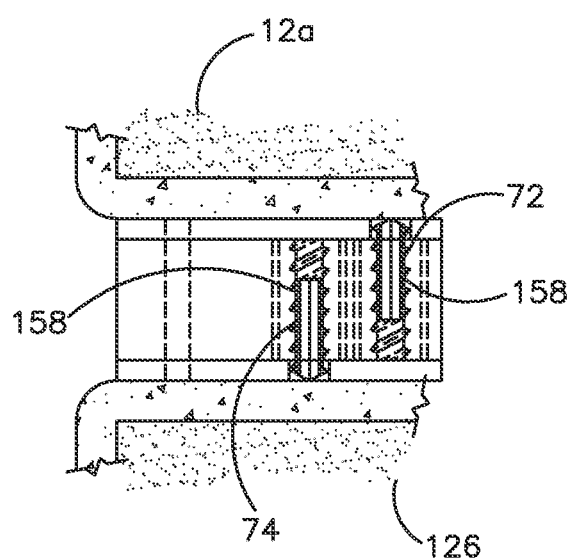
FIG. 13C is a side elevation view of the intervertebral implant as illustrated in FIG. 13B, having portions removed for the purposes of clarity.

Referring now to FIGS. 13A-C, the fixation assembly 22 of the implant 10 is illustrated in accordance with an alternative embodiment, whereby the fixation housing 36 includes a pair of laterally spaced fixation housing segments 36a and 36b that are connected to the lateral sides 32 and 34 of the implant body 20. Each housing segment 36a and 36b defines an aperture 63 that receives an actuator 40 illustrated as a shaft 89 in the manner described above. The shafts 89 can each be configured as a worm gear 155 having a corresponding helical gear tooth 157 that extends longitudinally about the circumference 141 of the shaft 89.

Figure 13D:
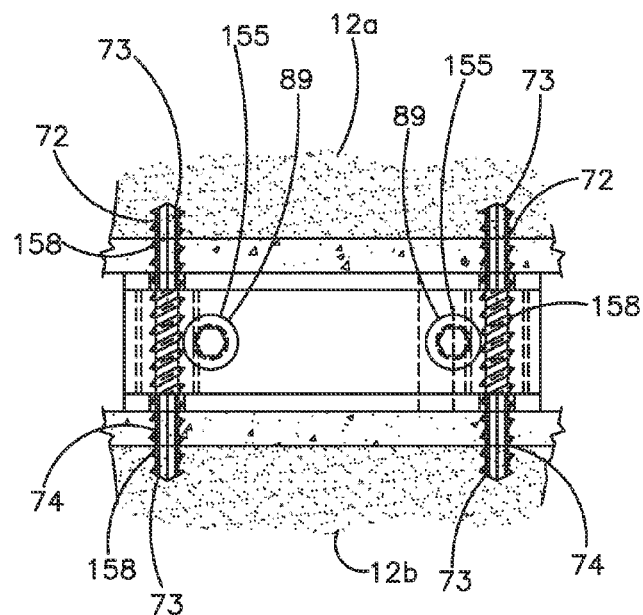
FIG. 13D is a front elevation view of the intervertebral implant as illustrated in FIG. 13B, showing the fixation assembly in an extended position.
Figures 13E, 13F:
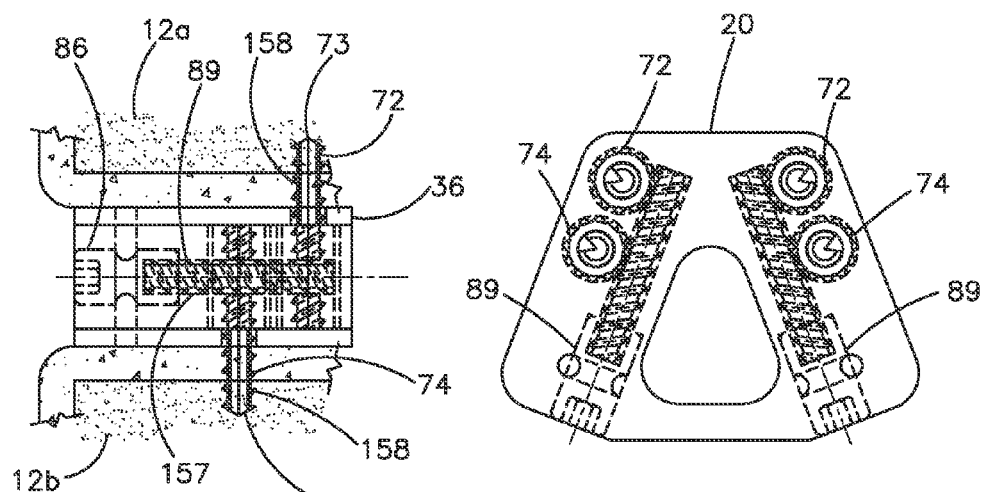
FIG. 13E is a side elevation view of the intervertebral implant as illustrated in FIG. 13D, having portions removed for the purposes of clarity.
FIG. 13F is a schematic top plan view of an intervertebral implant similar to the intervertebral implant as illustrated in FIG. 13A, but constructed in accordance with an alternative embodiment.

The fixation assembly 22 can further include at least one fixation member 38 illustrated as a first superior pin 72 having a tip 73 that faces transversely down, and a second inferior pin 74 having a tip 73 that faces transversely up. The pins 72 and 74 can each include a helical gear tooth 158 that is configured to mate with the gear teeth 157 of the respective shafts 89. The pins 72 and 74 are disposed in corresponding first and second superior and inferior channels 64 and 65, respectively, that extend transversely in the fixation housing 36. During operation, the shaft 89 can be disposed in a first disengaged position whereby the tips 73 are recessed in the fixation housing 36 and thus do not extend into the adjacent vertebral bodies 12a and 12b when the implant 10 is disposed in the intervertebral space 10. Referring to FIGS. 13D-E, the shaft 89 can be rotated to the engaged position, which causes the worm gear 155 to drive the gear tooth 158, thereby causing the pins 72 and 74 to translate transversely superiorly and inferiorly, respectively, until the tips 73 are inserted into the respective vertebral bodies 12a and 12b. The tips 73 can include cutting flutes and/or can be threaded as desired in the manner described above to enhance fixation in the vertebral bodies 12a and 12b.

As illustrated in FIG. 13A, the shafts 89 can extend substantially parallel to each other in the respective fixation housing segments 36a and 36b. Alternatively, as illustrated in FIG. 13F, the shafts 89 can be angularly offset with respect to each other. For instance, the channels shafts 89 can converge toward each other along a direction from their proximal ends to their distal ends as illustrated in FIG. 3F. Alternatively still, the shafts 89 can diverge away from each other along a direction from their proximal ends to their distal ends.

Figure 14A:
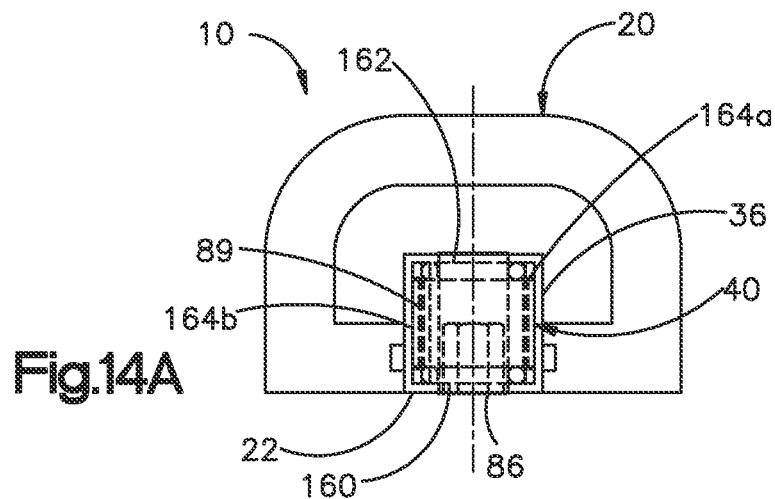
FIG. 14A is a top plan view of an intervertebral implant including an implant body and a fixation assembly constructed in accordance with an alternative embodiment, having portions removed for the purposes of clarity, showing the fixation assembly in a retracted position.
Figure 14B:
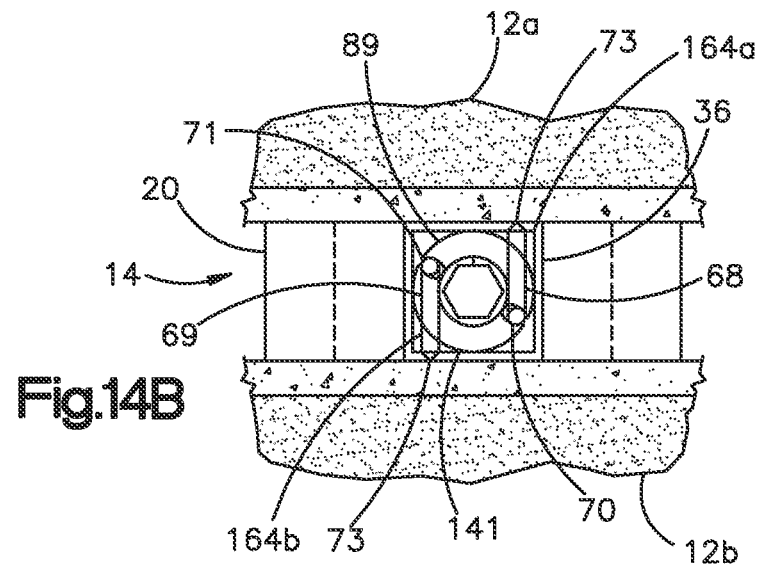
FIG. 14B is a front elevation view of the intervertebral implant as illustrated in FIG. 14A, having portions removed for the purposes of clarity, shown in an intervertebral space.

Referring now to FIGS. 14A-B, the fixation assembly 22 can include the rotatable shaft 89 supported in the fixation housing 36 substantially as described above with respect to FIGS. 11A-C. Thus, the fixation assembly 22 includes an actuator 40 in the form of a rotatable shaft 89 that is connected to the fixation housing 36 so as to be rotatable with respect to the fixation housing 36 and translatably fixed to the fixation housing 36. The rotatable shaft 89 can be threaded or unthreaded, and can be configured so as to maintain a substantially fixed longitudinal position (and thus does not substantially translate proximally or distally) as it rotates relative to the fixation housing 36. The shaft 89 defines an engagement member illustrated as a socket 86 that extends longitudinally into the proximal end of the shaft 89. The socket 86 is illustrated as a hexagonal in shape, though it could be shaped as any suitable polygonal shape, including a "plus" shape, a "dash" shape, or any alternative shape as desired so as to receive a drive member that actuates the shaft to rotate.

The shaft 89 can define a proximal surface 160 and a distal surface 162, and at least one bore that extends longitudinally through the shaft 89 between the proximal and distal surfaces 162. The shaft 89 can include a first superior bore 164a and a second inferior bore 164b that extends through the shaft at a location 180 degrees offset with respect to the first bore 164a. The fixation assembly 22 can include at least fixation member 38 in the form of a first superior staple 68 and a second inferior staple 69. The first staple 68 includes a base in the form of a crossbar 70 and at least a first pair of laterally spaced pins 72 that extend out from the crossbar 70 at any location, such as at opposed outer ends of the crossbar 70 as illustrated. The second staple 69 can further include a second pair of laterally spaced pins 74 that extend out from base illustrated as a second crossbar 71 at any location, such as at opposed outer ends of the crossbar 71 as illustrated.

The crossbars 70 and 71 of the staples 68 and 69 can extend longitudinally through the first and second bores 164a and 164b, respectively. The crossbars 70 and 71 can be loosely received in the first and second bores 164a and 164b such that the crossbars 70 and 71 are rotatable inside the bores 164a and 164b. Thus, the staples 68 and 69 and associated pins 72 and 74 can pivot relative to the shaft 89 about a longitudinal pivot axis defined by the crossbars 70 and 71, respectively. It can thus be said that the pins 72 and 74 are connected to the shaft 89 at a location inwardly spaced with respect to the outer circumference 141 of the shaft 89. The pins 72 and 74 extend out from the crossbars 70 and 71 and the shaft 89 along a substantially transverse direction in respective superior and inferior channels 64 and 65. The pins 72 and 74 can be flexible or rigid as desired, and can extend along the adjacent proximal and distal shaft surfaces so as to fix the staples 68 and 69 with respect to translation relative to the shaft 89.

Figure 14C:
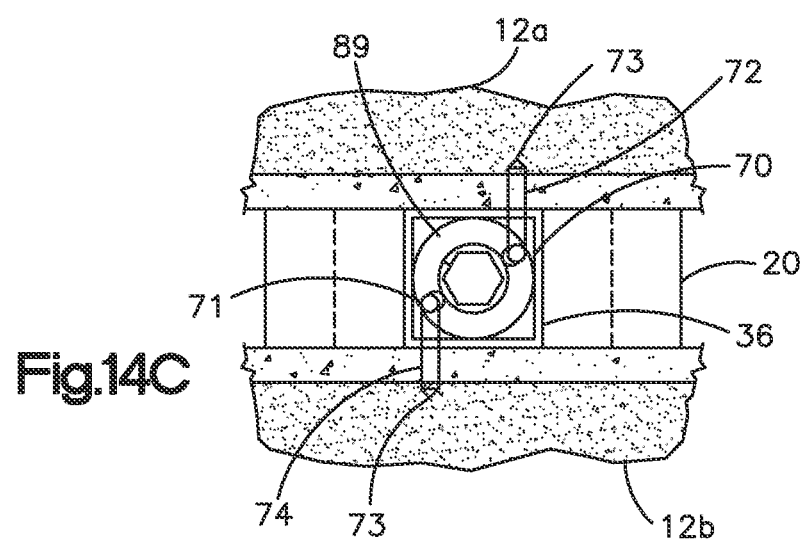
FIG. 14C is a front elevation view of the intervertebral implant as illustrated in FIG. 14B, showing the fixation assembly in an extended position.

Referring also to FIG. 14C, during operation, the shaft 89 rotates from a first rotational disengaged position whereby the staples 68 and 69 are in the recessed position to an second rotational engaged position whereby the staples 68 and 69 are in the extended position. The staples 68 and 69 can travel in their respective channels 64 as they move from their retracted positions to their extended positions. As the shaft 89 rotates about a longitudinal axis from the disengaged position to the engaged position, the pins 72 and 74 can pivot about a longitudinal axis so as to remain substantially transversely oriented as the tips 73 project out from the fixation housing 36 and into the adjacent vertebral bodies 12a and 12b. When the staples 68 and 69 are in the retracted positions, the tips 63 are disposed in the housing 36 and do not extend into the respective vertebral bodies 12a and 12b. The fixation housing 36 can provide any suitable stop that prevents the shaft 89 from over-rotating past the engaged position. It should be appreciated that the shaft 89 can be rotated in an opposite direction from the engaged position to the disengaged position so as to cause the staples 68 and 69 to retract from the extended position to the retracted position.

It should be noted that, unless otherwise specified, the term "or" is used in its nonexclusive form (e.g. "A or B" includes A, B, A and B, or any combination thereof, but does not have to include all of these possibilities). It should be noted that, unless otherwise specified, "and/or" is used similarly (e.g. "A and/or B" includes A, B, A and B, or any combination thereof, but does not have to include all of these possibilities). It should be noted that, unless otherwise specified, the term "includes" means "comprises" (e.g. a device that includes or comprises A and B contains A and B but optionally may contain C or additional components other than A and B). It should be noted that, unless otherwise specified, the singular forms "a," "an," and "the" refer to one or more than one, unless the context clearly dictates otherwise.

Although the invention has been described with reference to preferred embodiments or preferred methods, it is understood that the words which have been used herein are words of description and illustration, rather than words of limitation. For instance, it should be appreciated that while the intervertebral implant has been described herein as configured to fix to adjacent vertebral bodies, the implant can alternatively be inserted into a space between any bones or bone segments (e.g., fractured bone segments) as desired, and subsequently fixed to the adjacent bones or bone segments in the manner described herein. Furthermore, although the invention has been described herein with reference to particular structure, methods, and embodiments, the invention is not intended to be limited to the particulars disclosed herein, as the invention extends to all structures, methods and uses that are within the scope of the present invention. Unless otherwise indicated, the structure and features of various embodiments described herein can further be incorporated into the other embodiments described herein as desired. Accordingly, those skilled in the art will realize that the invention is intended to encompass all modifications and alternative arrangements included within the spirit and scope of the invention, for instance as set forth by the appended claims.

What is claimed:

1. An intervertebral implant configured to be fixed in an intervertebral space defined by a first vertebral body and a second vertebral body, the intervertebral implant comprising:
   an implant body sized to be inserted into an intervertebral space; and
   a fixation assembly configured to be attached to the implant body, the fixation assembly including:
      a housing defining a first vertebral body facing surface and a second vertebral body facing surface spaced from the first vertebral body facing surface along a transverse direction, and a proximal end and an opposed distal end that is spaced from the proximal end along a longitudinal direction angularly offset with respect to the transverse direction;
      at least one fixation member supported by the housing and movable from a retracted position along a direction having a longitudinal directional component to an extended position, whereby in the extended position the fixation member extends out from the housing and into one of the vertebral bodies; and
      an actuator configured to iterate the fixation member from the retracted position to the extended position, the actuator comprising a screw that threadedly engages the housing and is rotatable with respect to the housing so as to iterate the fixation member from the retracted position to the extended position;
      wherein the fixation member comprises a pair of fixation members, each defining a first terminal end that extends into the first vertebral body and a second terminal end that extends into the second vertebral body when the fixation members are in the extended position.

2. The intervertebral implant as recited in claim 1, wherein the housing defines a channel that extends along a direction having both transverse and longitudinal directional components; and the fixation member is movable in the channel from the retracted position to the extended position.

3. The intervertebral implant as recited in claim 2, wherein the channel is curved.

4. The intervertebral implant as recited in claim 1, wherein the fixation member is flexible.

5. The intervertebral implant as recited in claim 1, wherein when the fixation member is in the extended position, an associated terminal end of the fixation member extends out from the housing in a substantially transverse orientation.

6. The intervertebral implant as recited in claim 1, wherein the fixation member is entirely recessed in the housing in the retracted position.

7. The intervertebral implant as recited in claim 1, wherein the screw translates longitudinally with respect to the housing when the screw is rotated relative to the housing.

8. The intervertebral implant as recited in claim 1, wherein the fixation member defines a proximal end that is fixed to the screw with respect to translation relative to the screw, and rotatable with respect to the screw.

9. The intervertebral implant as recited in claim 1, wherein the fixation member is rotatably coupled to the screw so as to rotate along with the screw.

10. The intervertebral implant as recited in claim 1, wherein the housing is integral with the implant body.

11. The intervertebral implant as recited in claim 1, wherein the housing defines a channel that extends along a direction having both transverse and longitudinal directional components; and the fixation member is movable in the channel from the retracted position to the extended position.

12. The intervertebral implant as recited in claim 11, wherein the channel is curved.

13. An intervertebral implant configured to be fixed in an intervertebral space defined by a first vertebral body and a second vertebral body, the intervertebral implant comprising:
   an implant body sized to be inserted into an intervertebral space; and
   a fixation assembly configured to be attached to the implant body, the fixation assembly including:
      a housing defining a first vertebral body facing surface and a second vertebral body facing surface spaced from the first vertebral body facing surface along a transverse direction, and a proximal end and an opposed distal end that is spaced from the proximal end along a longitudinal direction angularly offset with respect to the transverse direction;
      at least one fixation member supported by the housing and movable from a retracted position along a direction having a longitudinal directional component to an extended position, whereby in the extended position the fixation member extends out from the housing and into one of the vertebral bodies; and
      an actuator configured to iterate the fixation member from the retracted position to the extended position, the actuator comprising a screw that threadedly engages the housing and is rotatable with respect to the housing so as to iterate the fixation member from the retracted position to the extended position;
      wherein the fixation member defines a proximal end that is fixed to the screw with respect to translation relative to the screw, and rotatable with respect to the screw.

14. The intervertebral implant as recited in claim 13, wherein the fixation member is flexible.

15. The intervertebral implant as recited in claim 13, wherein when the fixation member is in the extended position, a terminal end of the fixation member extends out from the housing in a substantially transverse orientation.

16. The intervertebral implant as recited in claim 13, wherein the fixation member is entirely recessed in the housing in the retracted position.

17. The intervertebral implant as recited in claim 13, wherein the screw translates longitudinally with respect to the housing when the screw is rotated relative to the housing.

18. The intervertebral implant as recited in claim 13, wherein the fixation member is rotatably coupled to the screw so as to rotate along with the screw.

19. The intervertebral implant as recited in claim 13, wherein the housing is integral with the implant body.

20. An intervertebral implant configured to be fixed in an intervertebral space defined by a first vertebral body and a second vertebral body, the intervertebral implant comprising:
   an implant body sized to be inserted into an intervertebral space; and
   a fixation assembly configured to be attached to the implant body, the fixation assembly including:
      a housing defining a first vertebral body facing surface and a second vertebral body facing surface spaced from the first vertebral body facing surface along a transverse direction, and a proximal end and an opposed distal end that is spaced from the proximal end along a longitudinal direction angularly offset with respect to the transverse direction;
      at least one fixation member supported by the housing and movable from a retracted position along a direction having a longitudinal directional component to an extended position, whereby in the extended position the fixation member extends out from the housing and into one of the vertebral bodies; and
      an actuator configured to iterate the fixation member from the retracted position to the extended position
      wherein the fixation member comprises a pair of fixation members, each defining a first terminal end that extends into the first vertebral body and a second terminal end that extends into the second vertebral body when the fixation members are in the extended position.

21. The intervertebral implant as recited in claim 20, wherein the housing defines a channel that extends along a direction having both transverse and longitudinal directional components; and the fixation member is movable in the channel from the retracted position to the extended position.

22. The intervertebral implant as recited in claim 21, wherein the channel is curved.

23. The intervertebral implant as recited in claim 20, wherein the fixation member is flexible.

24. The intervertebral implant as recited in claim 20, wherein when the fixation member is in the extended position, an associated terminal end of the fixation member extends out from the housing in a substantially transverse orientation.

25. The intervertebral implant as recited in claim 20, wherein the fixation member is entirely recessed in the housing in the retracted position.

26. The intervertebral implant as recited in claim 20, wherein the actuator comprises a screw that threadedly engages the housing and is rotatable with respect to the housing so as to iterate the fixation member from the retracted position to the extended position, wherein the screw translates longitudinally with respect to the housing when the screw is rotated relative to the housing.

27. The intervertebral implant as recited in claim 20, wherein the actuator comprises a screw that threadedly engages the housing and is rotatable with respect to the housing so as to iterate the fixation member from the retracted position to the extended position, wherein the fixation member is rotatably coupled to the screw so as to rotate along with the screw.

28. The intervertebral implant as recited in claim 20, wherein the housing is integral with the implant body.

29. An intervertebral implant configured to be fixed in an intervertebral space defined by a first vertebral body and a second vertebral body, the intervertebral implant comprising:
   an implant body sized to be inserted into an intervertebral space; and
   a fixation assembly configured to be attached to the implant body, the fixation assembly including:
      a housing defining a first vertebral body facing surface and a second vertebral body facing surface spaced from the first vertebral body facing surface along a transverse direction, and a proximal end and an opposed distal end that is spaced from the proximal end along a longitudinal direction angularly offset with respect to the transverse direction;
      at least one fixation member supported by the housing and movable from a retracted position along a direction having a longitudinal directional component to an extended position, whereby in the extended position the fixation member extends out from the housing and into one of the vertebral bodies; and an actuator configured to iterate the fixation member from the retracted position to the extended position;
wherein the fixation member defines a proximal end that is fixed to the actuator with respect to translation relative to the actuator, and rotatable with respect to the actuator.

30. The intervertebral implant as recited in claim 29, wherein the housing defines a channel that extends along a direction having both transverse and longitudinal directional components; and the fixation member is movable in the channel from the retracted position to the extended position.

31. The intervertebral implant as recited in claim 30, wherein the channel is curved.

32. The intervertebral implant as recited in claim 29, wherein the fixation member is flexible.

33. The intervertebral implant as recited in claim 29, wherein when the fixation member is in the extended position, a terminal end of the fixation member extends out from the housing in a substantially transverse orientation.

34. The intervertebral implant as recited in claim 29, wherein the fixation member is entirely recessed in the housing in the retracted position.

35. The intervertebral implant as recited in claim 29, wherein the actuator comprises a screw that threadedly engages the housing and is rotatable with respect to the housing so as to iterate the fixation member from the retracted position to the extended position, wherein the screw translates longitudinally with respect to the housing when the screw is rotated relative to the housing.

36. The intervertebral implant as recited in claim 29, wherein the actuator comprises a screw that threadedly engages the housing and is rotatable with respect to the housing so as to iterate the fixation member from the retracted position to the extended position, wherein the fixation member is rotatably coupled to the screw so as to rotate along with the screw.

37. The intervertebral implant as recited in claim 29, wherein the actuator comprises a screw that threadedly engages the housing and is rotatable with respect to the housing so as to iterate the fixation member from the retracted position to the extended position, wherein the housing is integral with the implant body.

* * * * *